United States Patent
Kugler et al.

(10) Patent No.: US 11,730,055 B2
(45) Date of Patent: Aug. 15, 2023

(54) DOPANT, CHARGE TRANSFER SALT AND ORGANIC ELECTRONIC DEVICE

(71) Applicants: Cambridge Display Technology Limited, Godmanchester (GB); Sumitomo Chemical Company Limited, Tokyo (JP)

(72) Inventors: Thomas Kugler, Godmanchester (GB); Sheena Zuberi, Godmanchester (GB); Florence Bourcet, Godmanchester (GB); Jean-Benoit Giguere, Godmanchester (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 1337 days.

(21) Appl. No.: 16/063,671

(22) PCT Filed: Dec. 16, 2016

(86) PCT No.: PCT/GB2016/053967
§ 371 (c)(1),
(2) Date: Jun. 18, 2018

(87) PCT Pub. No.: WO2017/103610
PCT Pub. Date: Jun. 22, 2017

(65) Prior Publication Data
US 2020/0274072 A1    Aug. 27, 2020

(30) Foreign Application Priority Data

Dec. 18, 2015 (GB) ..................... 1522439
Feb. 19, 2016 (GB) ..................... 1602925
(Continued)

(51) Int. Cl.
*H10K 85/60* (2023.01)
*C07D 235/18* (2006.01)
(Continued)

(52) U.S. Cl.
CPC ....... *H10K 85/6572* (2023.02); *C07D 235/18* (2013.01); *C08G 61/02* (2013.01);
(Continued)

(58) Field of Classification Search
None
See application file for complete search history.

(56) References Cited

U.S. PATENT DOCUMENTS 5,179,467 A    1/1993    Buchwalter et al.
8,920,944 B2   12/2014   Limmert et al.
(Continued)

FOREIGN PATENT DOCUMENTS

EP    0 431 547 A    6/1991
EP    2 738 194 A1   6/2014
(Continued)

OTHER PUBLICATIONS

English text machine translation of the Description and Claims of Geum et al. (KR 2013-0086733 A) accessed online from Espacenet; attached as a PDF, pp. 1-30. (Year: 2013).*
(Continued)

*Primary Examiner* — Katie L. Hammer
(74) *Attorney, Agent, or Firm* — Wolf, Greenfield & Sacks, P.C.

(57) ABSTRACT

A compound of formula (I): (Core)n-(X)m wherein Core is a core group; n is 0 and m is 1, or n is 1 and m is at least 1; and X is a group of formula (II): wherein: $R^1$, $R^3$ and $R^5$ are each independently H or a substituent; $R^2$ and $R^4$ are each a substituent; one of $R^1$-$R^5$ is a direct bond or divalent
(Continued)

linking group linking the group of formula (II) to Core in the case where n is 1; x and y are 0, 1, 2, 3 or 4; and the compound of formula (I) is substituted with at least one ionic substituent. The compound may be used as an n-dopant to dope an organic semiconductor.

(Core)n—(X)m   (I)

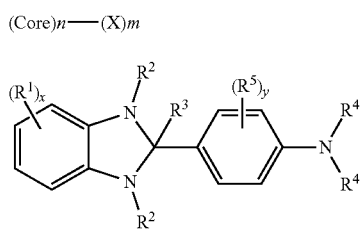

(II)

15 Claims, 10 Drawing Sheets

(30) Foreign Application Priority Data

Feb. 19, 2016 (GB) .................................... 1602928
Jul. 29, 2016 (WO) ................ PCT/GB2016/053967

(51) Int. Cl.
| | |
|---|---|
| C08G 61/02 | (2006.01) |
| H10K 85/10 | (2023.01) |
| C09K 11/06 | (2006.01) |
| C08L 101/02 | (2006.01) |
| H01B 1/12 | (2006.01) |
| H10K 50/17 | (2023.01) |
| H10K 71/00 | (2023.01) |
| H10K 71/15 | (2023.01) |
| H10K 71/40 | (2023.01) |
| H10K 101/30 | (2023.01) |
| H10K 102/10 | (2023.01) |

(52) U.S. Cl.
CPC .......... *C08L 101/025* (2013.01); *C09K 11/06* (2013.01); *H01B 1/128* (2013.01); *H10K 85/115* (2023.02); *H10K 85/611* (2023.02); *C08G 2261/143* (2013.01); *C08G 2261/148* (2013.01); *C08G 2261/1424* (2013.01); *C08G 2261/1426* (2013.01); *C08G 2261/3142* (2013.01); *C08G 2261/514* (2013.01); *C08G 2261/95* (2013.01); *H10K 50/171* (2023.02); *H10K 71/00* (2023.02); *H10K 71/15* (2023.02); *H10K 71/441* (2023.02); *H10K 2101/30* (2023.02); *H10K 2102/103* (2023.02)

(56) References Cited

U.S. PATENT DOCUMENTS 9,133,130 B2 * 9/2015 Wei ..................... H01L 51/0047
2011/0240980 A1 * 10/2011 Wei ..................... C07D 235/18
977/734
2011/0248267 A1 10/2011 Wei et al.
2012/0256296 A1 10/2012 Wei et al.
2014/0070178 A1 3/2014 Lee et al.

FOREIGN PATENT DOCUMENTS

| EP | 2 869 348 A1 | 5/2015 |
|---|---|---|
| GB | 2 513 378 A | 10/2014 |
| JP | H02-169575 A | 6/1990 |
| JP | H02-294009 A | 12/1990 |
| JP | 2004-002703 A | 1/2004 |
| JP | 2004-059899 A | 2/2004 |
| JP | 2006-176755 A | 7/2006 |
| KR | 10-2013-0086733 A | 8/2013 |
| WO | WO 2006/060654 A2 | 6/2006 |
| WO | WO 2007/126929 A2 | 11/2007 |
| WO | WO 2008/029155 A2 | 3/2008 |
| WO | WO 2010/088419 A2 | 8/2010 |
| WO | WO 2012/133229 A1 | 10/2012 |
| WO | WO 2012/152366 A1 | 11/2012 |
| WO | WO 2013/098648 A1 | 7/2013 |
| WO | WO 2013/122182 A1 | 8/2013 |
| WO | WO 2014/133141 A1 | 9/2014 |

OTHER PUBLICATIONS

Japanese Office Action dated Nov. 4, 2020 in connection with Japanese Application No. 2018-531173.
International Search Report and Written Opinion for International Application No. PCT/GB2016/052347, dated Oct. 10, 2016.
International Search Report and Written Opinion for International Application No. PCT/GB2016/053967, dated May 22, 2017.
Combined Search and Examination Report for British Application No. 1522439.7, dated Jul. 29, 2016.
Combined Search and Examination Report for British Application No. 1602925.8, dated Dec. 21, 2016.
Combined Search and Examination Report for British Application No. 1602928.2, dated Dec. 21, 2016.
[No Author Listed] Database WPI Accession No. 1990-242935. 1990, 6 pages.
[No Author Listed] Database WPI Accession No. 1991-024983. 1991, 6 pages.
Ferraris et al., Performance evaluation of poly 3-(phenylthiophene) derivatives as active materials for electrochemical capacitor applications. Chem Mater. Nov. 1, 1998;10(11):3528-35.
Lin et al., Conjugated copolymers comprised cyanophenyl-substituted spirobifluorene and tricarbazole-triphenylamine repeat units for blue-light-emitting diodes. Journal of Polymer Science Part A: Polymer Chemistry. Dec. 7, 2009;48(2):292-301.
Naab et al., Mechanistic study on the solution-phase n-doping of 1,3-Dimethyl-2-aryl-2,3-dihydro-1 H-benzoimidazole derivatives. Journal of the American Chemical Society. Oct. 9, 2013;135(40):15018-25.
Shi et al., Toward high performance n-type thermoelectric materials by rational modification of BDPPV backbones. J Am Chem Soc. 2015; 137:6979-82.
Wei et al., Use of a 1 H-benzoimidazole derivative as an n-type dopant and to enable air-stable solution-processed n-channel organic thin-film transistors. J Am Chem Soc. Jul. 7, 2010;132(26):8852-3.
JP 2018-531173, Nov. 4, 2020, Office Action.

* cited by examiner

DOPANT, CHARGE TRANSFER SALT AND ORGANIC ELECTRONIC DEVICE

RELATED APPLICATIONS

This application is a national stage filing under 35 U.S.C. 371 of International Patent Application Serial No. PCT/GB2016/053967, filed Dec. 16, 2016, which is a Box VI priority of International Patent Application Serial No. PCT/GB2016/052347, filed Jul. 29, 2016, which claims priority to United Kingdom patent applications number GB 1602925.8, filed Feb. 19, 2016, United Kingdom patent application number GB 1602928.2, filed Feb. 19, 2016, and United Kingdom patent application number GB 1522439.7, filed Dec. 18, 2015, each of which is incorporated herein by reference in its entirety.

FIELD OF THE INVENTION

The invention relates to n-doped organic semiconductors, methods of forming n-doped semiconductors and organic electronic devices containing n-doped semiconductors.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An organic light-emitting device has a substrate carrying an anode, a cathode and an organic light-emitting layer containing a light-emitting material between the anode and cathode.

In operation, holes are injected into the device through the anode and electrons are injected through the cathode. Holes in the highest occupied molecular orbital (HOMO) and electrons in the lowest unoccupied molecular orbital (LUMO) of the light-emitting material combine to form an exciton that releases its energy as light.

Cathodes include a single layer of metal such as aluminium, a bilayer of calcium and aluminium as disclosed in WO 98/10621; and a bilayer of a layer of an alkali or alkali earth compound and a layer of aluminium as disclosed in L. S. Hung, C. W. Tang, and M. G. Mason, Appl. Phys. Lett. 70, 152 (1997).

An electron-transporting or electron-injecting layer may be provided between the cathode and the light-emitting layer.

Bao et al, "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852-8853 discloses doping of [6,6]-phenyl $C_{61}$ butyric acid methyl ester (PCBM) by mixing (4-(1,3-dimethyl-2,3-dihydro-1H-benzoimidazol-2-yl)phenyl)dimethylamine (N-DMBI) with PCBM and activating the N-DMBI by heating.

US 2014/070178 discloses an OLED having a cathode disposed on a substrate and an electron-transporting layer formed by thermal treatment of an electron-transporting material and N-DMBI. It is disclosed that a radical formed on thermal treatment of N-DMBI may be a n-dopant.

U.S. Pat. No. 8,920,944 discloses n-dopant precursors for doping organic semiconductive materials.

Naab et al, "Mechanistic Study on the Solution-Phase n-Doping of 1,3-Dimethyl-2-aryl-2,3-dihydro-1H-benzoimidazole Derivatives", J. Am. Chem. Soc. 2013, 135, 15018-15025 discloses that n-doping may occur by a hydride transfer pathway or an electron transfer pathway.

It is an object of the invention to provide an organic electronic device comprising a solution-processed, n-doped layer.

SUMMARY OF THE INVENTION

In a first aspect the invention provides a compound of formula (I):

$$(\text{Core})n\text{-}(X)m \quad (I)$$

wherein Core is a core group; n is 0 and m is 1, or n is 1 and m is at least 1; and X is a group of formula (II):

wherein:
$R^1$, $R^2$, $R^3$, $R^4$ and $R^5$ are each independently H or a substituent;
one of $R^1$-$R^5$ is a direct bond or divalent linking group linking the group of formula (II) to Core in the case where n is 1;
x is 0, 1, 2, 3 or 4;
y is 0, 1, 2, 3 or 4; and
the compound of formula (I) is substituted with at least one ionic substituent.

In a second aspect the invention provides a polymer having a backbone substituted with side groups comprising groups of formula (II):

wherein:
$R^1$, $R^2$, $R^{3'}$ $R^4$ and $R^5$ are each independently H or a substituent, with the proviso that at least one occurrence of at least one of $R^1$-$R^5$ is a substituent comprising an ionic group;
one of $R^1$-$R^5$ is a direct bond or divalent linking group linking the group of formula (II) to the polymer backbone;
x is 0, 1, 2, 3 or 4; and
y is 0, 1, 2, 3 or 4.

In a third aspect the invention provides a composition comprising an organic semiconductor and a compound or polymer according to any one of the preceding claims.

In a fourth aspect the invention provides a formulation comprising a composition according to the third aspect and at least one solvent.

In a fifth aspect the invention provides a charge transfer salt formed by doping an organic semiconductor with a compound or polymer according to the first or second aspect.

In a sixth aspect the invention provides an organic electronic device comprising a layer comprising a charge-transfer salt according to the fifth aspect.

In a seventh aspect the invention provides a method of forming a layer of an organic electronic device comprising the step of depositing a formulation comprising a compound or polymer comprising an n-dopant substituted with at least one ionic substituent and an organic semiconductor dissolved in one or more polar solvents onto a surface and evaporating the one or more polar solvents.

DESCRIPTION OF THE DRAWINGS

The invention will now be described in more detail with reference to the drawings in which.

DETAILED DESCRIPTION OF THE INVENTION

Figure 1:
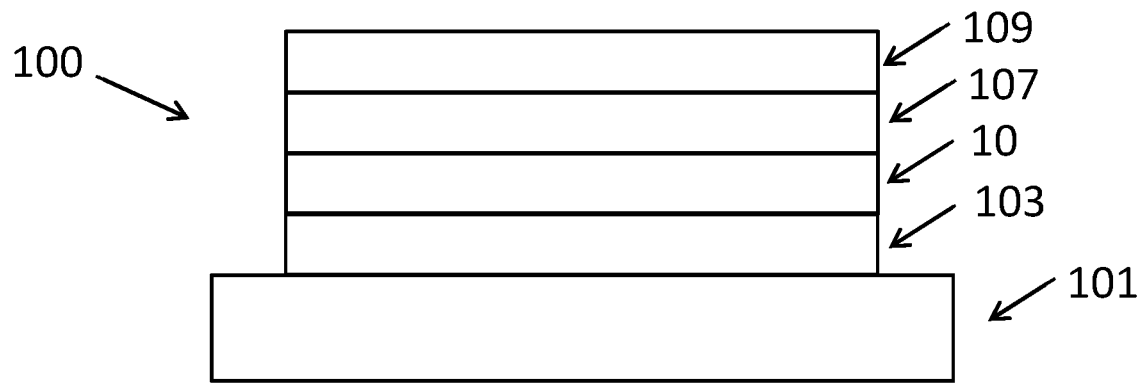
FIG. 1 illustrates schematically an OLED according to an embodiment of the invention.

FIG. 1, which is not drawn to any scale, illustrates an OLED 100 according to an embodiment of the invention supported on a substrate 101, for example a glass or plastic substrate. The OLED 100 comprises an anode 103, a light-emitting layer 105, an electron-injecting layer 107 and a cathode 109.

The anode 103 may be single layer of conductive material or may be formed from two or more conductive layers. Anode 103 may be a transparent anode, for example a layer of indium-tin oxide. A transparent anode 103 and a transparent substrate 101 may be used such that light is emitted through the substrate. The anode may be opaque, in which case the substrate 101 may be opaque or transparent, and light may be emitted through a transparent cathode 109.

Light-emitting layer 105 contains at least one light-emitting material. Light-emitting material 105 may consist of a single light-emitting compound or may be a mixture of more than one compound, optionally a host doped with one or more light-emitting dopants. Light-emitting layer 105 may contain at least one light-emitting material that emits phosphorescent light when the device is in operation, or at least one light-emitting material that emits fluorescent light when the device is in operation. Light-emitting layer 105 may contain at least one phosphorescent light-emitting material and at least one fluorescent light-emitting material.

Electron-injecting layer 107 comprises or consists of a charge-transfer complex formed from an organic semiconductor doped by an n-dopant of formula (I), or a polymer comprising n-dopants in a sidechain thereof.

Cathode 109 is formed of at least one layer, optionally two or more layers, for injection of electrons into the device.

Preferably, the electron-injecting layer 107 is in contact with organic light-emitting layer 105. Preferably, the film comprising the organic semiconductor and n-dopant is formed directly on organic light-emitting layer 105.

Preferably, the organic semiconductor has a LUMO that is no more than about 1 eV, optionally less than 0.5 eV or 0.2 eV, deeper (i.e. further from vacuum) than a LUMO of a material of the light-emitting layer, which may be a LUMO of a light-emitting material or a LUMO of a host material if the light-emitting layer comprises a mixture of a host material and a light-emitting material. Optionally, the doped organic semiconductor has a work function that is about the same as a LUMO of a material of the light-emitting layer. Optionally, the organic semiconductor has a LUMO of less (i.e. closer to vacuum) than 3.0 eV from vacuum level, optionally around 2.1 to 2.8 eV from vacuum level. Preferably, the organic semiconductor has a LUMO level of up to 2.2 or 2.3 eV below the vacuum level.

Preferably, the cathode 109 is in contact with the electron-injecting layer 107.

Preferably, the cathode is formed directly on the film comprising the organic semiconductor and n-dopant.

The OLED 100 may be a display, optionally a full-colour display wherein the light-emitting layer 105 comprises pixels comprising red, green and blue subpixels.

The OLED 100 may be a white-emitting OLED. White-emitting OLEDs as described herein may have a CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K. A white-emitting OLED may contain a plurality of light-emitting materials, preferably red, green and blue light-emitting materials, more preferably red, green and blue phosphorescent light-emitting materials, that combine to produce white light. The light-emitting materials may all be provided in light-emitting layer 105, or one or more additional light-emitting layers may be provided.

A red light-emitting material may have a photoluminescence spectrum with a peak in the range of about more than 550 up to about 700 nm, optionally in the range of about more than 560 nm or more than 580 nm up to about 630 nm or 650 nm.

A green light-emitting material may have a photoluminescence spectrum with a peak in the range of about more than 490 nm up to about 560 nm, optionally from about 500 nm, 510 nm or 520 nm up to about 560 nm.

A blue light-emitting material may have a photoluminescence spectrum with a peak in the range of up to about 490 nm, optionally about 450-490 nm.

The photoluminescence spectrum of a material may be measured by casting 5 wt % of the material in a PMMA film onto a quartz substrate and measuring in a nitrogen environment using apparatus C9920-02 supplied by Hamamatsu.

The OLED 100 may contain one or more further layers between the anode 103 and the cathode 109, for example one or more charge-transporting, charge-blocking or charge-injecting layers. Preferably, the device comprises a hole-injection layer comprising a conducting material between the anode and the light emitting layer 105. Preferably, the device comprises a hole-transporting layer comprising a semiconducting hole-transporting material between the anode 103 and the light emitting layer 105.

The electron-injecting layer is formed by doping an organic semiconductor acceptor material with the n-dopant.

The n-dopant may spontaneously dope the acceptor material to form a charge-transfer salt, or n-doping may occur upon activation, for example heat or irradiation of the n-dopant and acceptor. The electron-injecting layer may comprise or consist of the charge-transfer salt.

In forming the electron-injecting layer, the organic semiconductor and n-dopant may be deposited in air.

In forming the electron-injecting layer, the organic semiconductor and n-dopant may be deposited from a solution in a solvent or solvent mixture. The solvent or solvent mixture may be selected to prevent dissolution of the underlying layer, such as an underlying organic light-emitting layer 105 or the underlying layer may be crosslinked. The or each solvent is preferably a polar solvent.

In one embodiment, the n-dopant has formula (I):

wherein Core is a core group; n is 0 and m is 1, or n is 1 and m is at least 1; and X is a group of formula (II):

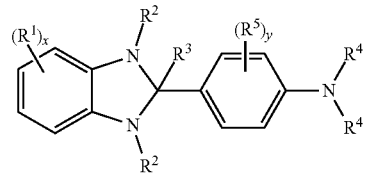

wherein:
$R^1$, $R^2$, $R^3$ $R^4$ and $R^5$ are each independently H or a substituent;
x and y are each independently 0, 1, 2, 3 or 4;
one of $R^1$-$R^5$ is a direct bond or divalent linking group linking the group of formula (II) to Core in the case where n is 1; and
the compound of formula (I) is substituted with at least one ionic substituent.

"Ionic substituent" as used herein means a substituent that comprises or consists of an ionic group.

Exemplary ionic groups have formula (III):

wherein $Sp^1$ is a spacer group; A is an anion or cation; p is 0 or 1; q is 1 if p is 0; and q is at least 1, preferably 1, if p is 1, the compound further comprising one or more counterions B to balance the charge of the one or more anions or cations A.

Optionally, $Sp^1$ is selected from:
$C_{1-10}$ alkylene wherein one or more non-adjacent C atoms may be replace with O, S, C=O, COO or phenylene; and arylene or heteroarylene, preferably phenylene, that may be unsubstituted or substituted with one or more $C_{1-20}$ alkyl groups wherein one or more non-adjacent C atoms of the $C_{1-20}$ alkyl groups may be replaced with O, S, C=O or COO.

"$C_{1-10}$ alkylene" as used herein means a divalent carbon atom or divalent alkyl chain.

Optionally, arylene or heteroarylene groups of $Sp^1$ are selected from phenylene and 5 or 6 membered heteroarylene groups. Substituents of arylene or heteroarylene groups of $Sp^1$ are optionally selected from $C_{1-20}$ alkyl, optionally $C_{1-12}$ alkyl wherein one or more non-adjacent C atoms may be replaced with O, S, C=O or COO, preferably 0.

A of formula (III) and B may have the same valency, with a counterion B balancing the charge of each A of formula (III).

Anion or cation A may be monovalent or polyvalent.

Preferably, A and B are each monovalent.

In another embodiment, the compound of formula (I) may comprise a plurality of anions or cations A, preferably monovalent anions or cations A, wherein the charge of two or more anions or cations A is balanced by a single, polyvalent counterion B. Optionally, the compound of formula (I) comprises one or more di- or trivalent cations B.

Exemplary anions A may be selected from, without limitation, sulfonate and —COO$^-$. A preferred anion A is —COO$^-$.

Exemplary cations A may be selected from organic or inorganic cations including, without limitation —N(R$^{11}$)$_3^+$; —P(R$^{11}$)$_3^+$; S(R$^{11}$)$_2^+$; or a heteroaromatic cation, optionally a heteroaromatic cation comprising or consisting of C and N atoms optionally pyridinium or imidazolium, wherein R$^{11}$ in each occurrence is H or C$_{1-12}$ hydrocarbyl, optionally C$_{1-12}$ alkyl. A preferred cation A is —NR$^{11}_3{}^+$.

Cation B is optionally a metal cation, optionally Li$^+$, Na$^+$, K$^+$, Cs$^+$, preferably Cs$^+$, or an organic cation, optionally N(R$^{11}$)$_4{}^+$ such as tetraalkylammonium, or a heteroaromatic cation optionally ethylmethyl imidazolium or pyridinium. The size of the cation may affect the dopant strength of the n-dopant. Preferably, the cation is an organic cation or a metal cation from the third or higher periods of the Periodic Table, preferably fourth or higher periods, more preferably fifth or higher periods of the Periodic Table.

Anion B is optionally halide, optionally F—, Cl—, Br— or I—; hydroxide; a borate, optionally BF$_4{}^-$; a phosphate, optionally PF$_6{}^-$; a phosphinate; a phosphonate; an imide, optionally TFSI; or a sulfonate group, optionally mesylate, tosylate or sulfonate.

Any of R$^1$-R$^5$ may comprise or consist of an ionic group. The group of formula (II) has at least one ionic substituent, optionally two or more ionic substituents. If two or more ionic substituents are present then optionally two groups R$^1$ are ionic substituents and/or two groups R$^5$ are ionic substituents.

The compound of formula (I) may comprise one or more non-ionic substituents, for example a non-ionic substituent R$^1$-R$^9$ as described anywhere herein, with the proviso that the compound of formula (I) comprises at least one ionic substituent. Exemplary non-ionic substituents include C$_{1-20}$ alkyl wherein one or more non-adjacent, non-terminal C atoms are replaced with phenylene, O, S, COO or CO; and phenyl which may be unsubstituted or substituted by one or more C1-20 alkyl groups wherein one or more non-adjacent, non-terminal C atoms are replaced with phenylene, O, S, COO or CO. By "non-terminal C atom" is meant an atom of an alkyl chain other than the methyl group at the end or a n-alkyl chain or the methyl groups at the ends of a branched alkyl chain.

Preferably, R$^2$ is C$_{1-12}$ alkyl.

Preferably, R$^3$ is H.

R$^5$, if present, is optionally a C$_{1-20}$ hydrocarbyl group. Preferably, y is 0.

In the case where n=0, the group of formula (II) is a compound and at least one occurrence of at least one of R$^1$-R$^5$, preferably at least one occurrence of at least one of R$^1$ and R$^4$, is an ionic group.

In the case where R$^1$ is an ionic group, p of formula (III) is preferably 0.

In the case where R$^1$ is an ionic group, x of formula (II) is preferably 1.

In the case where R$^4$ is not an ionic group, it is preferably a C$_{1-20}$ hydrocarbyl group, preferably a C$_{1-12}$ alkyl group.

In the case where R$^4$ is an ionic group, p of formula (III) is preferably 1 and Sp$^1$ is preferably a C$_{1-12}$ alkylene group wherein one or more non-adjacent C atoms of the alkylene group may be replaced by O or COO.

In the case where n=0, the or each group R$^1$-R$^5$ that is not an ionic group or H is optionally selected from C$_{1-40}$ hydrocarbyl, optionally C$_{1-12}$ alkyl or C$_{6-20}$ aryl, optionally phenyl, that is unsubstituted or substituted with one or more C$_{1-12}$ alkyl groups.

In the case where n is 1, one of R$^1$-R$^5$ is a direct bond or divalent linking group linking the group of formula (II) to Core. The divalent linking group of the or each group of formula (II) is optionally selected from unsubstituted or substituted phenylene and C$_{1-12}$ alkylene wherein one or more non-adjacent C atoms of the alkylene may be replaced with O, S, CO or COO and one or more C atoms may be replaced with unsubstituted or substituted aryl or heteroaryl. Optionally, aryl or heteroaryl groups of the divalent linking group are selected from phenylene and 5 or 6 membered heteroarylene groups. Substituents of aryl or heteroaryl groups are optionally selected from C$_{1-12}$ alkyl.

Exemplary linking groups are phenylene; C$_{1-12}$ alkylene; phenylene-C$_{1-12}$ alkylene; and phenoxy-C$_{1-12}$ alkylene wherein each phenylene group may be unsubstituted or substituted with one or more C$_{1-12}$ alkyl groups.

In the case where n=1, the or each group R$^1$-R$^5$ that is not an ionic group, a linking group or H is optionally selected from C$_{1-40}$ hydrocarbyl, optionally C$_{1-12}$ alkyl or C$_{6-20}$ aryl, optionally phenyl, that is unsubstituted or substituted with one or more C$_{1-12}$ alkyl groups.

In the case where n is 1, Core is optionally substituted with one or more ionic groups in which case the or each group of formula (II) may or may not be substituted with one or more ionic substituents.

In the case where n is 1, Core is optionally not be substituted with any ionic groups in which case the or each group of formula (II) is substituted with one or more ionic substituents.

Core may be selected from groups of formula Ar$_z$ wherein Ar in each occurrence independently is a C$_{6-20}$ aryl group, optionally phenyl or fluorene, and z is at least 1, optionally 1-5. Ar may be unsubstituted; substituted with at least one ionic substituent; or substituted with at least one non-ionic substituent.

In the case where n is 1, the compound of formula (I) is preferably a compound of formula (Ia):

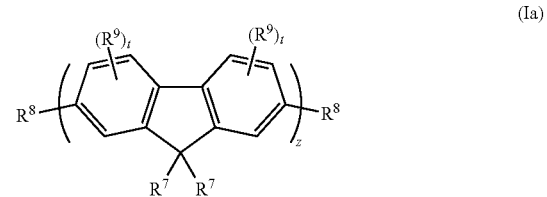

(Ia)

wherein R$^7$ in each occurrence is independently a substituent; R$^8$ independently in each occurrence is selected from H and a substituent; R$^9$ independently in each occurrence is a substituent; each t is independently 0, 1, 2 or 3; z is 1-5; and at least one occurrence of at least one of R$^7$, R$^8$ and R$^9$ is a group of formula (II).

Preferably, each t is 0.

Preferably, each R$^8$ is independently selected from H, an ionic substituent and a group of formula (II).

Preferably, each R$^7$ is independently selected from an ionic substituent and a group of formula (II).

The nature and/or position of the ionic group may affect the doping strength of the n-dopant. It will be appreciated that a cation A may have an electron-withdrawing effect whereas an anion A may have an electron-donating effect. Furthermore, the present inventors have surprisingly found that counterion B may also have an effect on dopant strength, and the size of the counterion may affect the dopant strength. The separation of the ionic group from the electron- or hydride-donor part of the n-dopant may have an effect. Accordingly, the nature and/or position of the ionic group may be selected to control a desired property of the n-dopant, for example its HOMO level. The ionic substituent may be selected and used to tune the properties of the n-dopant according to the organic semiconductor it is to be used with.

Exemplary compounds of formula (I) in the case where n=0 are:

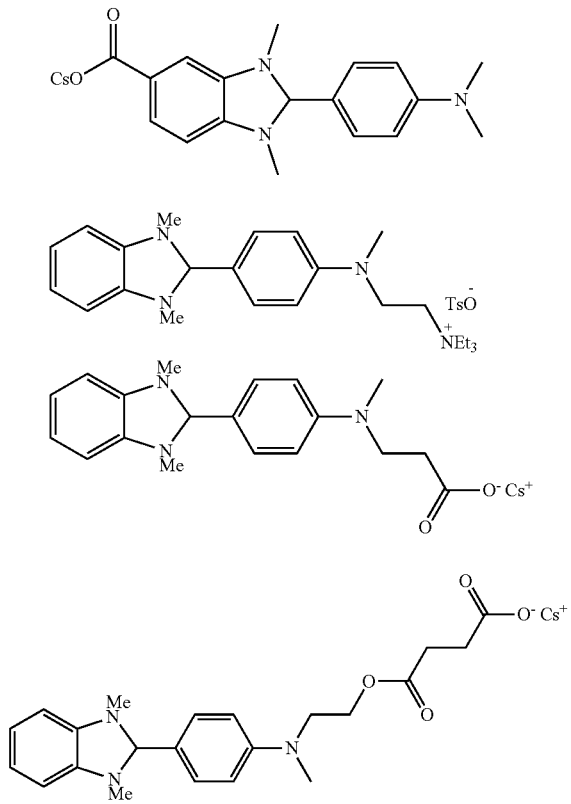

Exemplary compounds in the case where n is 1 are:

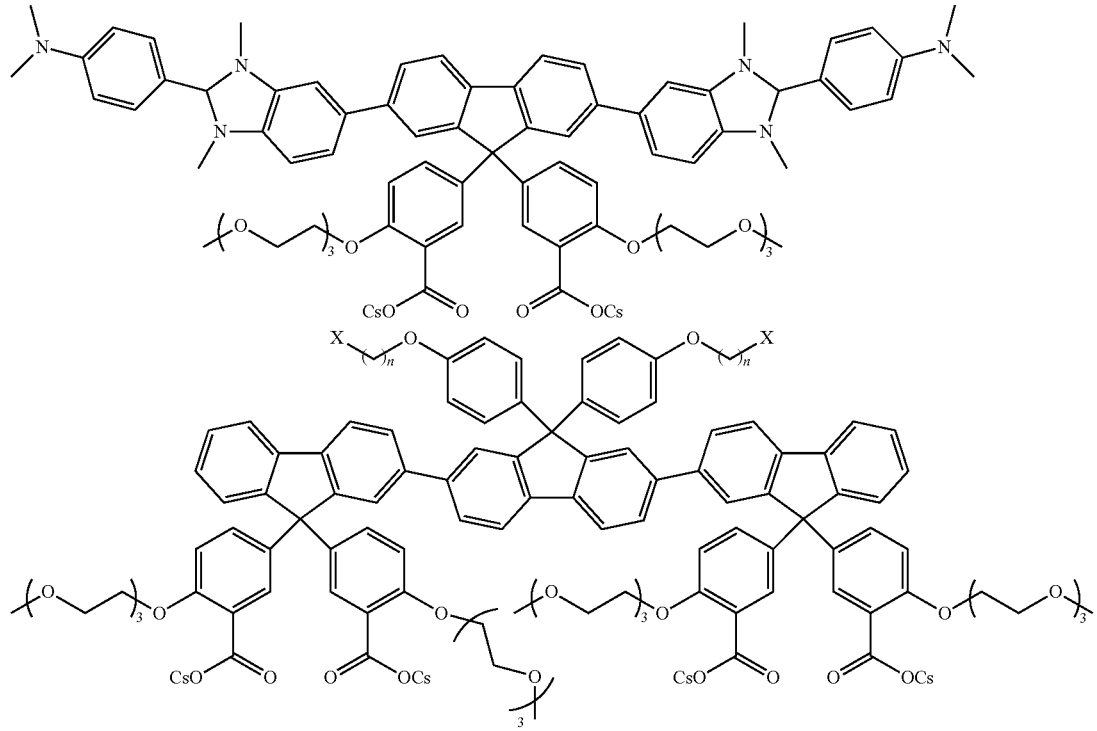

wherein n is 1-8 and wherein X independently in each occurrence is a group of formula (II) as described above.

The compounds of formula (I) are non-polymeric.

In another embodiment, n-dopant groups X of formula (II) are provided as a side-group of a polymer backbone. The polymer may comprise repeat units of formula (VIII):

(VIII)

wherein BG is a backbone group; $Sp^2$ is a spacer group; $R^6$ is a substituent; t is 0 or a positive integer; u is 0 or 1; v is 1 if u is 0; v is at least 1 if u is 1; w is at least 1; and X is a group of formula (II) as described above wherein of $R^1$-$R^5$ is a direct bond linking the group of formula (II) to $Sp^2$ in the case where u is 1 or to BG in the case where u is 0.

Optionally, $Sp^2$ is selected from the group consisting of $C_{1-20}$ alkylene, $C_{1-20}$ alkoxylene, $C_{1-20}$ oxyalkylene; phenylene-$C_{1-20}$ alkylene, phenylene-$C_{1-20}$ alkoxylene and phenylene-$C_{1-20}$ oxyalkylene wherein the phenylene group is unsubstituted or substituted, optionally substituted with one or more $C_{1-12}$ alkyl groups.

Substituents $R^6$ of formula (VIII), if present, may be the same or different in each occurrence and are optionally selected from the group consisting of:

D;

alkyl, optionally $C_{1-20}$ alkyl, wherein one or more non-adjacent C atoms may be replaced with a group selected from: $C_{6-20}$ aryl or $C_{6-20}$ arylene, optionally phenyl, that is unsubstituted or substituted with one or more substituents, 5-20 membered heteroaryl or 5-20 membered heteroarylene that is unsubstituted or substituted with one or more substituents, O, S, C=O or —COO; or a group of formula —(Ar$^1$)$_n$ wherein Ar$^1$ in each occurrence is independently a C$_{6-20}$ aryl or 5-20 membered heteroaryl group that is unsubstituted or substituted with one or more substituents and n is at least 1, optionally 1, 2 or 3.

An aryl, arylene, heteroaryl or heteroarylene group of a substituent R$^6$ may be unsubstituted or substituted with one or more substituents. Substituents, where present, may selected from C$_{1-20}$ alkyl wherein one or more non-adjacent C atoms may be replaced with O, S, C=O or —COO—, more preferably C$_{1-20}$ alkyl.

The polymer may be a conjugated or non-conjugated polymer. By "conjugated polymer" is meant a polymer comprising repeat units in the polymer backbone that are directly conjugated to adjacent repeat units.

In the case of a conjugated polymer, BG is optionally a C$_{6-20}$ arylene repeat unit.

The polymer may comprise repeat units of formula (VIII) and one or more co-repeat units, optionally one or more C$_{6-20}$ arylene co-repeat units, each of which may be unsubstituted or substituted with one or more substituents, optionally one or more substituents R$^6$.

Arylene groups BG and/or arylene co-repeat units include, without limitation, fluorene, phenylene, naphthalene, anthracene, indenofluorene, phenanthrene and dihydrophenanthrene repeat units.

Arylene groups BG and/or arylene co-repeat units may be selected from repeat units of formulae (IX)-(XII):

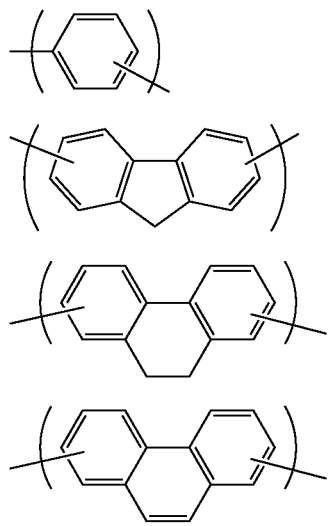

Repeat units of formulae (IX)-(XII) may have formulae (IXa)-(XIIa) respectively:

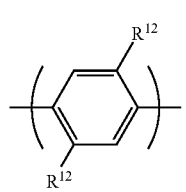

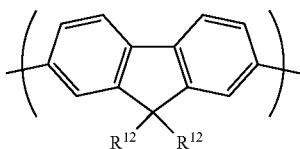

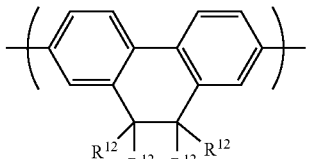

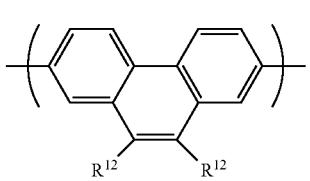

wherein R$^{12}$ in each occurrence is independently a group of formula -(Sp$^2$)u(X)v or a substituent R$^6$.

The substituent or substituents R$^6$ of a repeat unit of formula (VIII) and/or of a further repeat unit may be selected according to the required solubility of the polymer. Preferred substituents for solubility of the polymer in polar solvents are substituents containing one or more ether groups, optionally a substituent comprising a group of formula —(OCH$_2$CH$_2$)$_n$— wherein n is at least 1, optionally an integer from 1 to 10; groups of formula —COOR$^{10}$ wherein R$^{10}$ is a C$_{1-5}$ alkyl group; and ionic substituents. Ionic substituents R$^6$ may be cationic or anionic.

Exemplary anionic substituents comprise formula —COO$^-$ with a suitable metal or organic cation. Exemplary metal cations are alkali metal cations, preferably Cs+. Exemplary organic cations are ammonium, optionally tetraalkylammonium, ethylmethyl, imidazolium and pyridinium. Exemplary cationic substituents comprise quaternary ammonium with a suitable anion, optionally halide or sulfonate group, optionally mesylate, tosylate or sulfonate.

A polymer comprising ester substituents may be converted to a polymer comprising substituents formula —COO$^-$M$^+$. The conversion may be as described in WO 2012/133229, the contents of which are incorporated herein by reference.

Further substituents R$^6$ include C$_{1-40}$ hydrocarbyl groups, optionally C$_{1-20}$ alkyl; unsubstituted phenyl; and phenyl substituted with one or more C$_{1-12}$ alkyl groups.

The polymer may comprise an electron-accepting unit in its backbone, for example a repeat unit comprising benzothiadiazole; an arylene repeat unit substituted with one or more electron-withdrawing groups; or a repeat unit comprising a polar double or triple bond as described below. In this case, the n-dopant and acceptor are provide as part of the same polymer. It will therefore be understood that a "composition" of an n-dopant and an organic semiconductor as described herein includes a polymer comprising the n-dopant and organic semiconductor as well as a mixture of an organic semiconductor material that is separate from an n-dopant material, which may be a polymer substituted with n-dopants or a compound of formula (I).

Preferably, there is little or no spontaneous doping of the organic semiconductor upon contact with a group of formula (II). Preferably, the extent of n-doping in increased upon activation. Optionally, the n-dopant has a HOMO level that is the same as or, preferably, deeper (further from vacuum) than the LUMO level of the organic semiconductor, optionally at least 1 eV or 1.5 eV deeper than the LUMO level of the organic semiconductor. Accordingly, little or no spontaneous doping occurs upon mixing of the organic semiconductor and such an n-dopant at room temperature, and little or no spontaneous doping occurs between a polymer comprising acceptor units in a backbone thereof substituted with n-dopants.

Without wishing to be bound by any theory, n-doping by the group of formula (II) may be by a hydride transfer process as described in Naab et al, "Mechanistic Study on the Solution-Phase n-Doping of 1,3-Dimethyl-2-aryl-2,3-dihydro-1H-benzoimidazole Derivatives", J. Am. Chem. Soc. 2013, 135, 15018-15025, the contents of which are incorporated herein by reference.

The organic semiconductor:n-dopant weight ratio is optionally in the range 99:1-10:90.

Optionally the n-dopant:organic semiconductor molar ratio is greater than 50:50 in which case the n-dopant/organic semiconductor composition will comprise n-dopant that has not doped the organic semiconductor.

Organic Semiconductor

The organic semiconductor is n-doped by the n-dopant, either spontaneously on contact of the organic semiconductor and the n-dopant or upon activation. If no, or limited, spontaneous n-doping occurs then the extent of n-doping may be increased by activation.

The organic semiconductor may be a polymeric or non-polymeric material. Optionally, the organic semiconductor is a polymer, more preferably a conjugated polymer.

The organic semiconductor may comprise a polar double or triple bond, optionally a bond selected from a C=N (imino) group, a nitrile group, a C=S group, an oxime group or a C=O group, optionally a keto, ester or carbonate group. Preferably, these polar double- or triple-bond groups are conjugated to a conjugated polymer backbone. These polar double- or triple-bond groups may be provided as substituents of a conjugated repeat unit or may be part of a conjugated repeat unit, for example fluorenone.

The organic semiconductor may be a polymer comprising electron-deficient repeat units.

The organic semiconductor may comprise benzothiadiazole units. The benzothiadiazole units may be units of a polymer that is mixed with the polymer substituted with an n-dopant or a repeat unit in the backbone of the polymer substituted with an n-dopant. A polymeric repeat unit may comprise or consist of repeat units of formula:

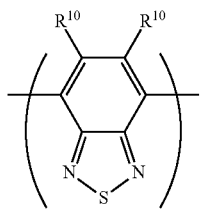

wherein $R^{10}$ in each occurrence is a substituent, optionally a substituent selected from alkyl, optionally $C_{1-20}$ alkyl, wherein one or more non-adjacent C atoms may be replaced with optionally substituted aryl or heteroaryl, O, S, C=O or —COO—, and one or more H atoms may be replaced with F.

A repeat unit comprising benzothiadiazole may have formula:

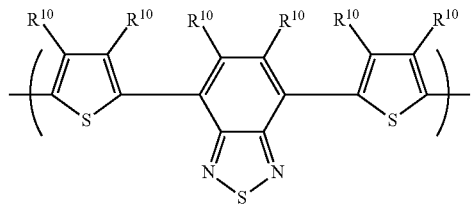

wherein $R^{10}$ is as described above with reference to benzothiadiazole.

The organic semiconductor may be a polymer comprising an arylene repeat unit substituted with one or more electron-withdrawing groups. An exemplary electron-withdrawing group is cyano.

Arylene repeat units include, without limitation, fluorene, phenylene, naphthalene, anthracene, indenofluorene, phenanthrene and dihydrophenanthrene repeat units, each of which may be substituted with one or more electron-withdrawing groups and optionally substituted with one or more further substituents. Exemplary further substituents, if present, may be selected from $C_{1-40}$ hydrocarbyl. Arylene repeat units may be selected from repeat units of formulae (IX)-(XII) as described above.

A polymer comprising an electron-deficient arylene repeat unit or a benzothiadiazole repeat unit may be a copolymer comprising one or more co-repeat units. The co-repeat units may be selected from arylene co-repeat units that are not substituted with an electron-withdrawing group and are optionally unsubstituted or substituted with one or more substituents selected from $C_{1-40}$ hydrocarbyl groups and ionic groups. Ionic groups may be as described with respect to formula (III).

Polymers as described anywhere herein, including polymers substituted with an n-dopant and semiconductor polymers, suitably have a polystyrene-equivalent number-average molecular weight (Mn) measured by gel permeation chromatography in the range of about $1 \times 10^3$ to $1 \times 10^8$, and preferably $1 \times 10^3$ to $5 \times 10^6$. The polystyrene-equivalent weight-average molecular weight (Mw) of polymers described anywhere herein may be $1 \times 10^3$ to $1 \times 10^8$, and preferably $1 \times 10^4$ to $1 \times 10$.

Polymers as described anywhere herein are suitably amorphous polymers.

Activation

In the case where the n-dopant does not dope the organic semiconductor spontaneously, n-doping may be effected by activation. Preferably, n-doping is effected after formation of a device comprising the layer containing the organic semiconductor and n-dopant, and optionally after encapsulation. Activation may be by excitation of the n-dopant and/or the organic semiconductor.

Exemplary activation methods are thermal treatment and irradiation.

Optionally, thermal treatment is at a temperature in the range 80° C. to 170° C., preferably 120° C. to 170° C. or 130° C. to 160° C.

Thermal treatment and irradiation as described herein may be used together.

For irradiation, any wavelength of light may be used, for example a wavelength having a peak in the range of about 200-700 nm.

Optionally, the peak showing strongest absorption in the absorption spectrum of the organic semiconductor is in the range of 400-700 nm. Preferably, the strongest absorption of the n-dopant is at a wavelength below 400 nm.

The present inventors have surprisingly found that exposure of a composition of an organic semiconductor and a polymer substituted with an n-dopant that does not spontaneously dope the organic semiconductor to electromagnetic radiation results in n-doping and that the electromagnetic radiation need not be at a wavelength that can be absorbed by the n-dopant.

The light emitted from the light source suitably overlaps with an absorption feature, for example an absorption peak or shoulder, of the organic semiconductor's absorption spectrum. Optionally, the light emitted from the light source has a peak wavelength within 25 nm, 10 nm or 5 nm of an absorption maximum wavelength of the organic semiconductor, however it will be appreciated that a peak wavelength of the light need not coincide with an absorption maximum wavelength of the organic semiconductor.

The extent of doping may be controlled by one or more of: the organic semiconductor/n-dopant ratio; the peak wavelength of the light; the duration of irradiation of the film; and the intensity of the light. It will be appreciated that excitation will be most efficient when a peak wavelength of the light coincides with an absorption maximum of the organic semiconductor.

Optionally, irradiation time is between 1 second and 1 hour, optionally between 1-30 minutes.

Preferably, the light emitted from the light source is in the range 400-700 nm. Preferably, the electromagnetic radiation has a peak wavelength greater than 400 nm, optionally greater than 420 nm, optionally greater than 450 nm. Optionally, there is no overlap between an absorption peak in the absorption spectrum of the n-dopant and the wavelength(s) of light emitted from the light source.

Any suitable electromagnetic radiation source may be used to irradiate the film including, without limitation, fluorescent tube, incandescent bulb and organic or inorganic LEDs. Optionally, the electromagnetic radiation source is an array of inorganic LEDs. The electromagnetic radiation source may produce radiation having one or more than one peak wavelengths.

Preferably, the electromagnetic radiation source has a light output of at least 2000 mW, optionally at least 3000 mW, optionally at least 4000 mW.

Preferably, no more than 10% or no more than 5% of the light output of the electromagnetic radiation source is from radiation having a wavelength less than or equal to 400 nm, optionally less than or equal to 420 nm. Preferably, none of the light output has a wavelength of less than or equal to 400 nm, optionally less than or equal to 420 nm.

Inducing n-doping without exposure to short wavelength light, such as UV light, may avoid damage to the materials of the OLED.

The n-doped organic semiconductor may be an extrinsic or degenerate semiconductor.

In manufacture of an organic electronic device, such as an OLED as described in FIG. 1, activation may take place during device formation or after the device has been formed. Preferably, activation to cause n-doping takes place after the device has been formed and encapsulated. The device may be manufactured in an environment in which little or no spontaneous doping occurs, for example a room temperature environment wherein the n-dopant and organic semiconductor are exposed to little or no wavelengths of light that induce n-doping until after encapsulation of the device, for example an environment illuminated by light having a longer wavelength than that of the electromagnetic radiation source such as a clean room illuminated with yellow light.

In the case of an OLED as described in FIG. 1, a film 107 of the polymer substituted with the n-dopant and the organic semiconductor may be formed over organic light-emitting layer 105 and the cathode 109 may be formed over the film.

For activation by irradiation, the film may then irradiated through the anode 101, in the case of a device formed on a transparent substrate 101 and having a transparent anode 103, such as ITO, or the film may be irradiated through the cathode 109 in the case of a device with a transparent cathode. The wavelength used to induce n-doping may be selected to avoid wavelengths that are absorbed by layers of the device between the electromagnetic radiation source and the film.

Light-Emitting Layers

The OLED 100 may contain one or more light-emitting layers.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12 1737-1750, 2000, the contents of which are incorporated herein by reference. Light-emitting layer 107 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission. A plurality of light-emitting layers may together produce white light.

A fluorescent light-emitting layer may consist of a light-emitting material alone or may further comprise one or more further materials mixed with the light-emitting material. Exemplary further materials may be selected from hole-transporting materials; electron-transporting materials and triplet-accepting materials, for example a triplet-accepting polymer as described in WO 2013/114118, the contents of which are incorporated herein by reference.

Cathode

The cathode may comprise one or more layers. Preferably, the cathode comprises or consists of a layer in contact with the electron injecting layer that comprises or consists of one or more conductive materials. Exemplary conductive materials are metals, preferably metals having a work function of at least 4 eV, optionally aluminium, copper, silver or gold or iron. Exemplary non-metallic conductive materials include conductive metal oxides, for example indium tin oxide and indium zinc oxide, graphite and graphene. Work functions of metals are as given in the CRC Handbook of Chemistry and Physics, 12-114, 87$^{th}$ Edition, published by CRC Press, edited by David R. Lide. If more than one value is given for a metal then the first listed value applies.

The cathode may be opaque or transparent. Transparent cathodes are particularly advantageous for active matrix devices because emission through a transparent anode in such devices is at least partially blocked by drive circuitry located underneath the emissive pixels.

It will be appreciated that a transparent cathode device need not have a transparent anode (unless a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Hole-Transporting Layer

A hole transporting layer may be provided between the anode 103 and the light-emitting layer 105.

The hole-transporting layer may be cross-linked, particularly if an overlying layer is deposited from a solution. The crosslinkable group used for this crosslinking may be a crosslinkable group comprising a reactive double bond such and a vinyl or acrylate group, or a benzocyclobutane group. Crosslinking may be performed by thermal treatment, preferably at a temperature of less than about 250° C., optionally in the range of about 100-250° C.

A hole transporting layer may comprise or may consist of a hole-transporting polymer, which may be a homopolymer or copolymer comprising two or more different repeat units. The hole-transporting polymer may be conjugated or non-conjugated. Exemplary conjugated hole-transporting polymers are polymers comprising arylamine repeat units, for example as described in WO 99/54385 or WO 2005/049546 the contents of which are incorporated herein by reference. Conjugated hole-transporting copolymers comprising arylamine repeat units may have one or more co-repeat units selected from arylene repeat units, for example one or more repeat units selected from fluorene, phenylene, phenanthrene naphthalene and anthracene repeat units, each of which may independently be unsubstituted or substituted with one or more substituents, optionally one or more $C_{1-40}$ hydrocarbyl substituents.

If present, a hole transporting layer located between the anode and the light-emitting layer 105 preferably has a HOMO level of 5.5 eV or shallower (closer to vacuum), more preferably around 4.8-5.5 eV or 5.1-5.3 eV as measured by square wave voltammetry. The HOMO level of the hole transport layer may be selected so as to be within 0.2 eV, optionally within 0.1 eV, of an adjacent layer in order to provide a small barrier to hole transport between these layers.

Preferably a hole-transporting layer, more preferably a crosslinked hole-transporting layer, is adjacent to the light-emitting layer 105.

A hole-transporting layer may consist essentially of a hole-transporting material or may comprise one or more further materials. A light-emitting material, optionally a phosphorescent material, may be provided in the hole-transporting layer.

A phosphorescent material may be covalently bound to a hole-transporting polymer as a repeat unit in the polymer backbone, as an end-group of the polymer, or as a side-chain of the polymer. If the phosphorescent material is provided in a side-chain then it may be directly bound to a repeat unit in the backbone of the polymer or it may be spaced apart from the polymer backbone by a spacer group. Exemplary spacer groups include $C_{1-20}$ alkyl and aryl-$C_{1-20}$ alkyl, for example phenyl-$C_{1-20}$ alkyl. One or more carbon atoms of an alkyl group of a spacer group may be replaced with O, S, C=O or COO.

Emission from a light-emitting hole-transporting layer and emission from light-emitting layer 105 may combine to produce white light.

Hole Injection Layers

A conductive hole injection layer, which may be formed from a conductive organic or inorganic material, may be provided between the anode 103 and the light-emitting layer 105 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Encapsulation

In the case where the polymer as described herein is substituted with an n-dopant that does not spontaneously dope the organic semiconductor, the n-dopant is preferably activated to cause n-doping as described herein after encapsulation of the device containing the film to prevent ingress of moisture and oxygen.

Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

The substrate on which the device is formed preferably has good barrier properties such that the substrate together with the encapsulant form a barrier against ingress of moisture or oxygen. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

Formulation Processing

Light-emitting layer 105 and electron-injecting layer 107 may be formed by any method including evaporation and solution deposition methods. Solution deposition methods are preferred.

Formulations suitable for forming light-emitting layer 105 and electron-injecting layer 107 may each be formed from the components forming those layers and one or more suitable solvents.

Preferably, light-emitting layer 105 is formed by depositing a solution in which the solvent is one or more non-polar solvent materials, optionally benzenes substituted with one or more substituents selected from $C_{1-12}$ alkyl and $C_{1-12}$ alkoxy groups, for example toluene, xylenes and methylanisoles, and mixtures thereof.

Optionally, the film comprising the organic semiconductor and the n-dopant to form the electron-injecting layer 107 is formed by depositing a solution.

Preferably, the electron-injecting layer is formed from a polar solvent, optionally a protic solvent, optionally water or an alcohol; dimethylsulfoxide; propylene carbonate; or 2-butanone which may avoid or minimise dissolution of the underlying layer if the materials of the underlying layer are not soluble in polar solvents. The ionic substituent or substituents of the compound of formula (I) or polymer comprising a group of formula (II) may provide enhanced solubility in polar solvents as compared to compounds without such ionic substituents. The organic semiconductor may also be substituted with polar substituents, optionally substituents of formula (III), to enhance its solubility in polar solvents.

Exemplary alcohols include methanol ethanol, propanol, butoxyethanol and monofluoro-, polyfluoro- or perfluoro-alcohols, optionally 2,2,3,3,4,4,5,5-Octafluoro-1-pentanol.

It will be appreciated that other n-dopants substituted with ionic substituents may be deposited using polar solvents. An example of such an n-dopant is NADH.

Particularly preferred solution deposition techniques including printing and coating techniques such spin-coating, inkjet printing and lithographic printing.

Coating methods are particularly suitable for devices wherein patterning of the light-emitting layer is unnecessary—for example for lighting applications or simple monochrome segmented displays.

Printing methods are particularly suitable for high information content displays, in particular full colour displays. A device may be inkjet printed by providing a patterned layer over the anode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, slot die coating, roll printing and screen printing.

Applications

The doped organic semiconductor layer has been described with reference to the electron-injection layer of an organic light-emitting device, however it will be appreciated that the layer formed as described herein may be used in other organic electronic device, for example as an electron-extraction layer of an organic photovoltaic device or organic photodetector; as an auxiliary electrode layer of a n-type organic thin film transistor or as an n-type semiconductor in a thermoelectric generator.

Measurements

UV-visible absorption spectra of pristine and n-doped acceptor materials as described herein were measured by spin-coating onto glass substrates, as blend with the dopant. The film thicknesses were in the range of 20-100 nm.

After spin-coating and drying, the polymer films were encapsulated in a glove box, in order to exclude any contact of the n-doped films with air.

After the encapsulation, UV-vis absorption measurements were conducted with a Carey-5000 Spectrometer, followed by successive exposures to visible light and repeat UV-VIS measurements.

HOMO, SOMO and LUMO levels as described anywhere herein are as measured by square wave voltammetry.

Equipment:
CHI660D Electrochemical workstation with software (IJ Cambria Scientific Ltd))
CHI 104 3 mm Glassy Carbon Disk Working Electrode (IJ Cambria Scientific Ltd))
Platinum wire auxiliary electrode
Reference Electrode (Ag/AgCl) (Havard Apparatus Ltd)
Chemicals

| | |
|---|---|
| Acetonitrile (Hi-dry anhydrous grade-ROMIL) | (Cell solution solvent) |
| Toluene (Hi-dry anhydrous grade) | (Sample preparation solvent) |
| Ferrocene - FLUKA | (Reference standard) |
| Tetrabutylammoniumhexafluorophosphate - FLUKA | (Cell solution salt) |

Sample Preparation

The acceptor polymers were spun as thin films (~20 nm) onto the working electrode; the dopant material was measured as a dilute solution (0.3 w %) in toluene.

Electrochemical Cell

The measurement cell contains the electrolyte, a glassy carbon working electrode onto which the sample is coated as a thin film, a platinum counter electrode, and a Ag/AgCl reference glass electrode. Ferrocene is added into the cell at the end of the experiment as reference material (LUMO (ferrocene)=−4.8 eV).

EXAMPLES

Compound Example 1

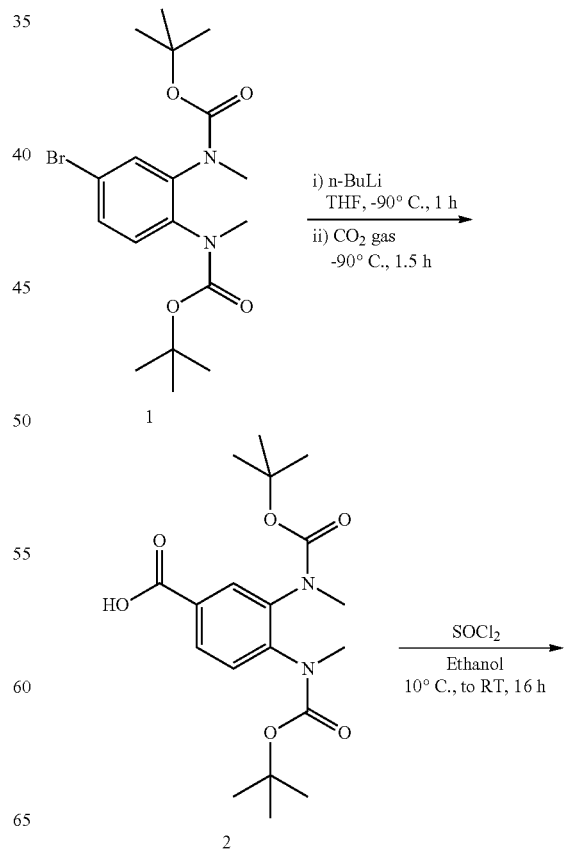

-continued

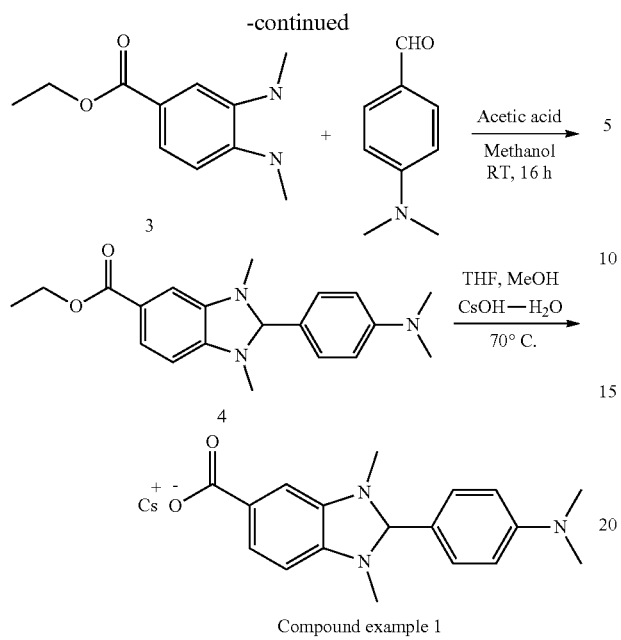

Compound example 1

Intermediate 2:

A solution of Intermediate 1 (23.6 g, 0.0568 mol) in tetrahydrofuran (120 ml) was cooled to −90° C. N-BuLi (2.5M in n-hexane, 34 ml, 0.0852 mol) was added slowly to the mixture at −90° C. and stirred for 1 hour at −90° C. Carbon dioxide gas was bubbled in the reaction mass for 1.5 hours at −90° C. Reaction mixture was allowed to warm up to room temperature slowly and quenched by adding water (150 ml). Organic layer was separated and aqueous layer was extracted with ethyl acetate (200 ml×2). Combined organic layer was washed with water (300 ml), brine (300 ml), dried over sodium sulfate and concentrated under reduce pressure. The crude material was adsorbed on celite and purified by column chromatography over silica gel using 3% methanol in chloroform as eluent to obtain 18 g of Intermediate 2 with 94.68% HPLC purity as a pale orange color viscous liquid, 65% yield.

$^1$H-NMR (400 MHz, DMSO D$_6$: δ [ppm] 1.36 (s, 18H), 3.32 (s, 6H), 7.39 (d, J=8 Hz, 1H), 7.76 (s, 1H) 7.83 (d, J=2.00 Hz, 1H)

Intermediate 3:

A solution of Intermediate 2 (18 g, 0.0473 mol) in ethanol (180 mL) was cooled to 0° C. and thionyl chloride (28.14 g, 0.236 mol) was added drop wise for 10 minutes. Reaction mixture was then stirred for 16 hours at room temperature. Reaction mixture was poured into ice (200 g), stirred for 30 minutes and basified by adding 10% aqueous sodium bicarbonate solution. The mixture was extracted with ethyl acetate (100 ml×3). Combined organic layers were washed with water (200 ml), brine (300 ml), dried over sodium sulfate and concentrated under reduced pressure. The crude material was adsorbed on celite and purified by column chromatography over silica gel (neutralized with triethyl amine) using 13% ethyl acetate in hexane as eluent to obtain 4.2 g Intermediate 3 with 99.32% HPLC purity as a pale orange color liquid, 42% yield.

$^1$H-NMR (400 MHz, CDCl$_3$): δ [ppm] 1.39 (t, J=7.20 Hz, 3H), 2.90 (s, 6H), 4.35 (q, J=6.80 Hz, 2H), 6.62 (d, J=8.4 Hz, 1H), 7.39 (s, 1H) 7.64 (d, J=2.00 Hz, 1H)

Intermediate 4:

Nitrogen was bubbled for 10 minutes into a solution of 4-N,N-Dimethyl amino benzaldehyde (3 g, 0.0201 mol) in anhydrous methanol (20 ml). Intermediate 3 (4.2 g, 0.0201 mol) was added and nitrogen bubbling continued for another 5 minutes. Glacial acetic acid (1 mL) was added and mixture was stirred at room temperature for 16 hours. The reaction was cooled to 0° C. and filtered. Solid was washed with cold methanol (10 ml) and dried to obtain 1.8 g fraction of Intermediate 4 with 99.01% HPLC purity as a white solid and 1.1 g fraction of Intermediate 4 with 97.51% HPLC purity as a white solid, 43% yield.

$^1$H-NMR (400 MHz, CDCl$_3$): δ [ppm] 1.37 (t, J=7.20 Hz, 3H), 2.57 (d, J=8.4 Hz, 6H), 2.98 (s, 6H), 4.3 (q, J=6.80 Hz, 2H), 5.09 (s, 1H), 6.36 (d, J=8.00 Hz, 1H), 6.82 (dd, J=1.6 Hz J=6.80 Hz, 2H), 6.9 (s, 1H), 7.37 (dd, J=2 Hz J=6.80 Hz, 2H), 7.46 (dd, J=1.6 Hz J=8.8 Hz, 1H)

Compound Example 1

Nitrogen was bubbled in a mixture of Intermediate 4 (5.000 g, 14.73 mmol) and tetrahydrofuran (25 ml) for 5 minutes followed by the addition of methanol (10 ml) and a solution of cesium hydroxide monohydrate (7.421 g, 44.19 mmol) in water (5 ml). Nitrogen was bubbled into the mixture for 10 minutes after which the mixture was heated to 70° C. for 16 hours. Once cooled, the mixture was evaporated to dryness under reduced pressure. The residue was dissolved in water and purified by column chromatography over C18 reversed phase silica, using a gradient of water to water:methanol 1:1 as eluent. The combined fractions containing Compound Example 1 were evaporated to dryness under reduced pressure and the residue was triturated with acetonitrile (100 ml), filtered and dried in a vacuum oven for 16 hours at 50° C. to afford 4.976 g of Compound Example 1 as a white powder at 99% purity by NMR, 76% yield.

$^1$H-NMR (600 MHz, MeOH-D$_4$): δ$_H$ [ppm] 2.51 (s, 3H), 2.53 (s, 3H), 2.95 (s, 6H), 4.77 (s, 1H), 6.34 (d, J=7.8 Hz, 1H), 6.79-6.81 (m, 2H), 7.04 (d, J=1.5 Hz, 2H), 7.36-7.39 (m, 2H), 7.41 (dd, J=7.8 Hz, J=1.6 Hz, 1H).

Compound Example 2

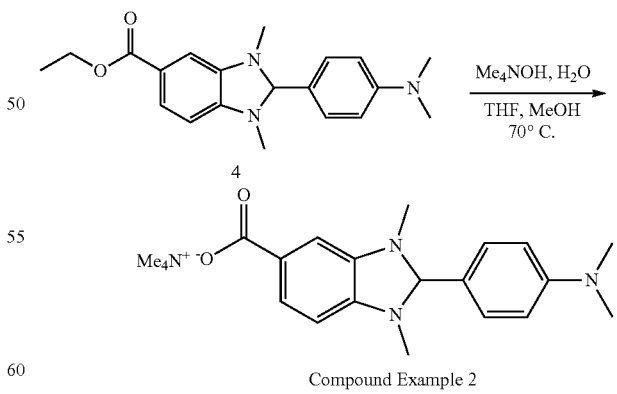

Compound Example 2

Nitrogen was bubbled in a mixture of Intermediate 4 (0.750 g, 2.21 mmol), tetrahydrofuran (10 ml) and Methanol (4 ml) for 5 minutes followed by the addition of a solution of tetramethylammonium hydroxide (10 wt % in water, 4.02 ml, 4.41 mmol). Nitrogen was bubbled in the mixture for 10 minutes after which the mixture was heated to 70° C. for 16 hours. Once cooled, the mixture was evaporated to dryness under reduced pressure. The residue was dissolved in water and purified by column chromatography over C18 reversed phase silica, using a gradient of water to water:methanol 1:1 as eluent. The combined fractions containing Compound Example 2 were evaporated to dryness under reduced pressure and the residue was triturated with acetonitrile (30 ml), filtered and dried in a vacuum oven for 16 hours at 50° C. to afford 0.627 g of Compound Example 2 as a white powder at 99% purity by NMR, 74% yield.

$^1$H-NMR (600 MHz, MeOH-D$_4$): $\delta_H$ [ppm] 2.52 (s, 3H), 2.54 (s, 3H), 2.97 (s, 6H), 3.17 (s, 12H), 4.78 (s, 1H), 6.35 (d, J=7.8 Hz, 1H), 6.80-6.82 (m, 2H), 7.05 (d, J=1.5 Hz, 2H), 7.37-7.39 (m, 2H), 7.42 (dd, J=7.4 Hz, J=1.5 Hz, 1H).

Compound Example 3

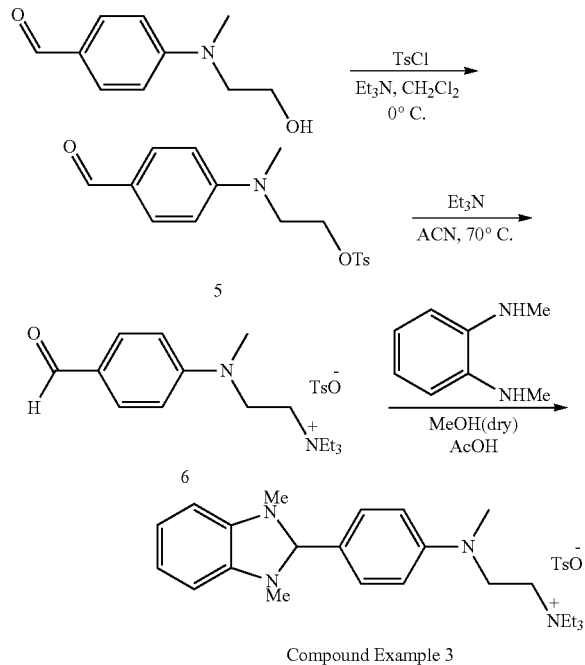

Intermediate 5:

N-Methyl-N-(2-hydroxyethyl)-4-aminobenzaldehyde (8.00 g, 44.6 mmol) was dissolved in dichloromethane (100 ml) and cooled to 0° C. Triethylamine (10.38 g, 14.2 ml, 102.7 mmol) was added and nitrogen was bubbled into the reaction mixture for 5 minutes. Tosylchloride (10.21 g, 53.57 mmol) was added portion wise over 20 minutes and the reaction was left to warm up to room temperature overnight. The reaction mixture was cooled to 0° C. and water (5 ml) was added drop wise followed by the drop wise addition of 10% aqueous HCl until pH 2 was reached. Water (50 ml) was added and the aqueous phase was extracted twice with dichloromethane. The organic phase was washed once with H$_2$O and twice with 3% aqueous NH$_4$OH, dried over magnesium sulfate and concentrated to dryness under reduced pressure. The crude product was filtered through a silica plug (Ø 70 mm×50 mm) using dichloromethane followed by dichloromethane:ethyl acetate (85:15). A first fraction was concentrated to dryness under reduced pressure, triturated with methanol (20 ml), filtered and air-dried to afford Intermediate 5 as a pink solid, 2.95 g, 99.14% pure by HPLC, 20% yield. The second fraction was concentrated to dryness under reduced pressure to afford Intermediate 5 as a pink solid, 7.72 g, 97.53% pure by HPLC, 52% yield.

$^1$H-NMR (600 MHz, CDCl$_3$): $\delta_H$ [ppm] 2.40 (s, 3H), 3.01 (s, 3H), 3.72 (t, J=6.0 Hz, 2H), 4.21 (d, J=5.8 Hz, 2H), 6.59 (d, J=9.0 Hz, 2H), 7.24 (d, J=8.2 Hz, 2H), 7.66-7.70 (m, 4H), 9.75 (s, 1H).

Intermediate 6

Nitrogen was bubbled in a mixture of Intermediate 5 (3.000 g, 8.99 mmol), acetonitrile (20 ml) and triethylamine (9.105 g, 89.9 mmol) for 5 minutes. The mixture was heated to reflux for 72 hours. Once cooled, the reaction mixture was poured into toluene (150 ml) and stirred for 30 minutes. The slurry was filtered and solid was dried in a vacuum oven at 50° C. for 16 hours to afford Intermediate 6 as an off-white solid, 3.00 g, 99% pure by NMR, 77% yield.

$^1$H-NMR (600 MHz, CDCl$_3$): $\delta_H$ [ppm] 1.29 (t, J=7.2 Hz, 9H), 2.28 (s, 3H), 3.08 (s, 3H), 3.36 (t, J=8.3 Hz, 2H), 3.47 (q, J=7.3 Hz, 6H), 3.99 (t, J=7.1 Hz, 2H), 6.71 (d, J=8.8 Hz, 2H), 7.07 (d, J=8.2 Hz0, 2H), 7.68-7.72 (m, 4H), 9.76 (s, 1H).

Compound Example 3

Nitrogen was bubbled in a solution of Intermediate 6 (0.680 g, 1.565 mmol) and N,N'-dimethyl-1,2-phenylenediamine (0.234 g, 1.72 mmol) in anhydrous methanol (2 ml) for 5 minutes. Acetic acid (0.05 ml) was added and nitrogen was bubbled into the reaction mixture for 5 mins. The mixture was stirred overnight at room temperature. Nitrogen was bubbled in a solution of sodium hydroxide (43 mg, 1.08 mmol) in water (5 ml) for 5 minutes. It was then added to the reaction mixture. The reaction mixture was purified by column chromatography over C18 reversed phase silica, using acetonitrile as eluent. The combined fractions containing Compound Example 3 were evaporated to dryness under reduced pressure. The residue was dissolved in water (50 ml), washed with toluene (2×20 ml) and extracted with dichloromethane (2×30 ml) under constant stream of nitrogen. The dichloromethane solution was concentrated to dryness under reduced pressure. The residue was dried in a vacuum oven at room temperature for 16 hours to afford Compound Example 3 as an off-white solid, 0.364 g, 99% pure by NMR, 42% yield.

$^1$H-NMR (600 MHz, CDCl$_3$) $\delta_H$ [ppm] 1.31 (t, J=7.4 Hz, 9H), 2.29 (s, 3H), 2.53 (s, 6H), 2.99 (s, 3H), 3.37 (t, J=7.6 Hz, 2H), 3.48 (q, J=7.4 Hz, 6H), 3.84 (t, J=7.0 Hz, 2H), 4.77 (s, 1H), 6.42-6.39 (m, 2H), 6.68-6.72 (m, 2H), 6.72-6.74 (m, 2H), 7.09 (d, J=7.8 Hz, 2H), 7.41-7.44 (m, 2H), 7.77 (d, J=8.1 Hz, 2H).

Compound Example 4

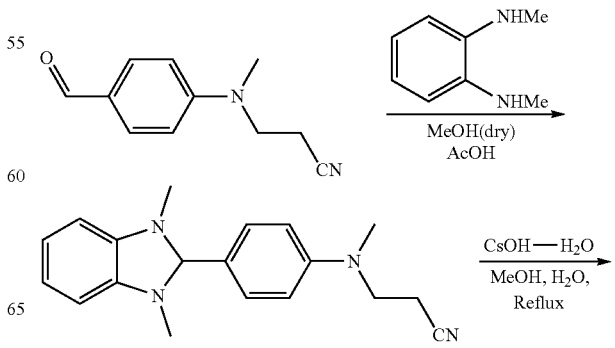

-continued

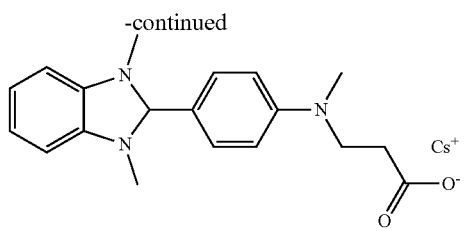

Compound Example 4

Nitrogen was bubbled in a solution of 4-[2-(cyanoethyl)methylamino]benzaldehyde (3.000 g, 15.93 mmol) and N,N'-Dimethyl-1,2-phenylenediamine (2.17 g, 15.93 mmol) in anhydrous tetrahydrofuran (5 ml) for 5 minutes. Methanol (6 ml) and acetic acid (0.15 ml) were added, nitrogen was bubbled into the reaction mixture for 10 minutes and the mixture was stirred for 16 hours at room temperature. Nitrogen was bubbled in a solution of cesium hydroxide monohydrate (8.02 g, 47.81 mmol) in water (10 ml) and isopropanol (15 ml) for 10 minutes. Hydroxide solution was added to the reaction mixture and heated to 90° C. for 24 hours. Once cooled, the reaction mixture was evaporated to dryness under reduced pressure. The residue was triturated with acetonitrile (30 ml) which was decanted off. The residue was dissolved in water and purified by column chromatography over C18 reversed phase silica, using a gradient of water to water:methanol 1:1 as eluent. The combined fractions containing Compound Example 4 were evaporated to dryness under reduced pressure. The residue was dried by evaporation to dryness under reduced pressure first by the addition of ethanol (50 ml) followed by acetonitrile (50 ml). The residue was dried in a vacuum oven at 50° C. for 16 hours to afford Compound Example 4 as an off-white solid, 2.23 g, 90% pure by NMR, 31% yield.

$^1$H-NMR (600 MHz MeOH-$D_4$): $\delta_H$ [ppm] 2.41 (t, J=7.5 Hz, 2H), 2.49 (s, 6H), 2.97 (s, 3H), 3.67 (t, J=7.5 Hz, 2H), 4.59 (s, 1H), 6.39-6.42 (m, 2H), 6.61-6.65 (m, 2H), 6.80 (d, J=8.7 Hz, 2H), 7.36 (d, J=8.6 Hz, 2H).

Compound Example 5

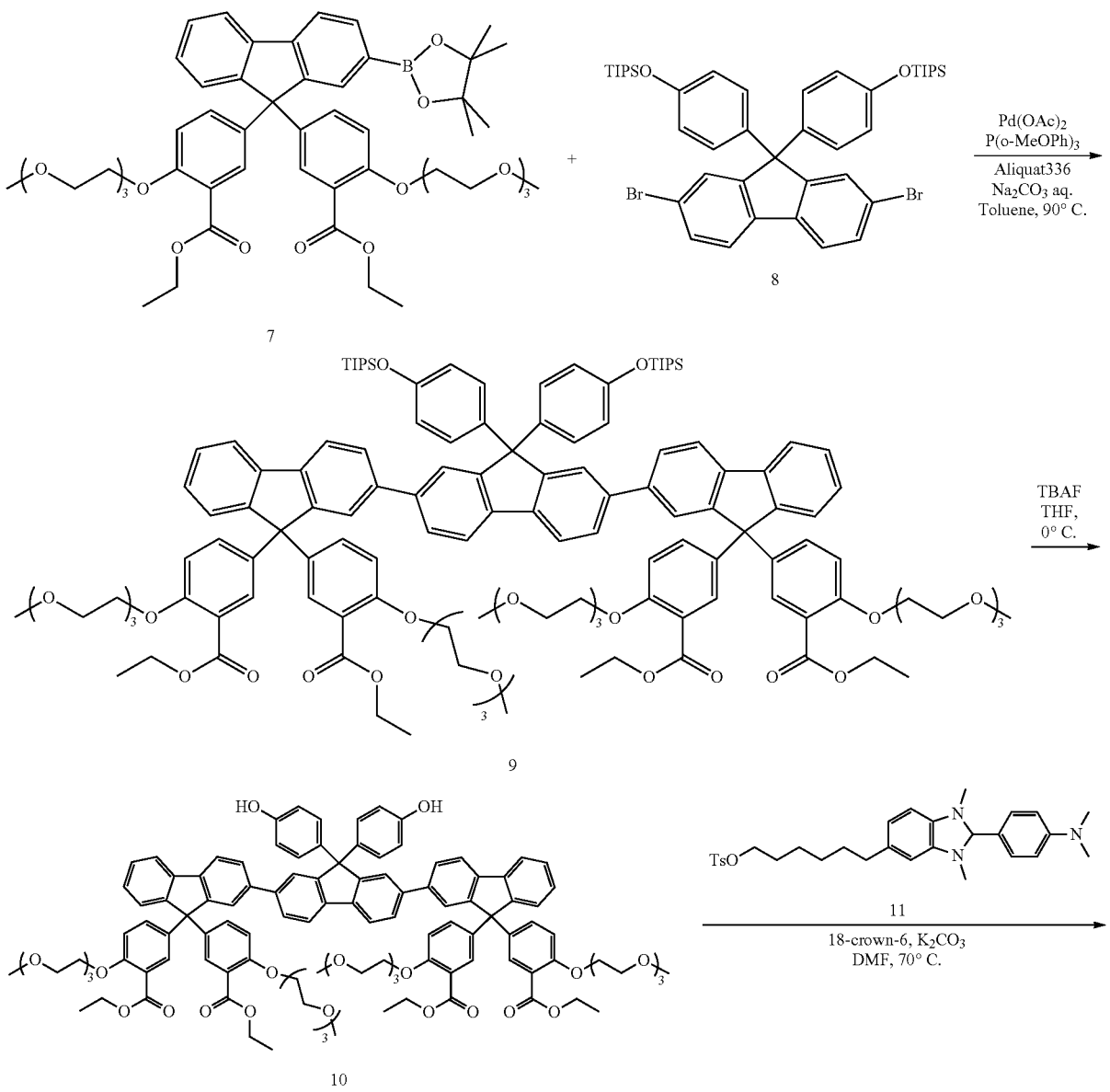

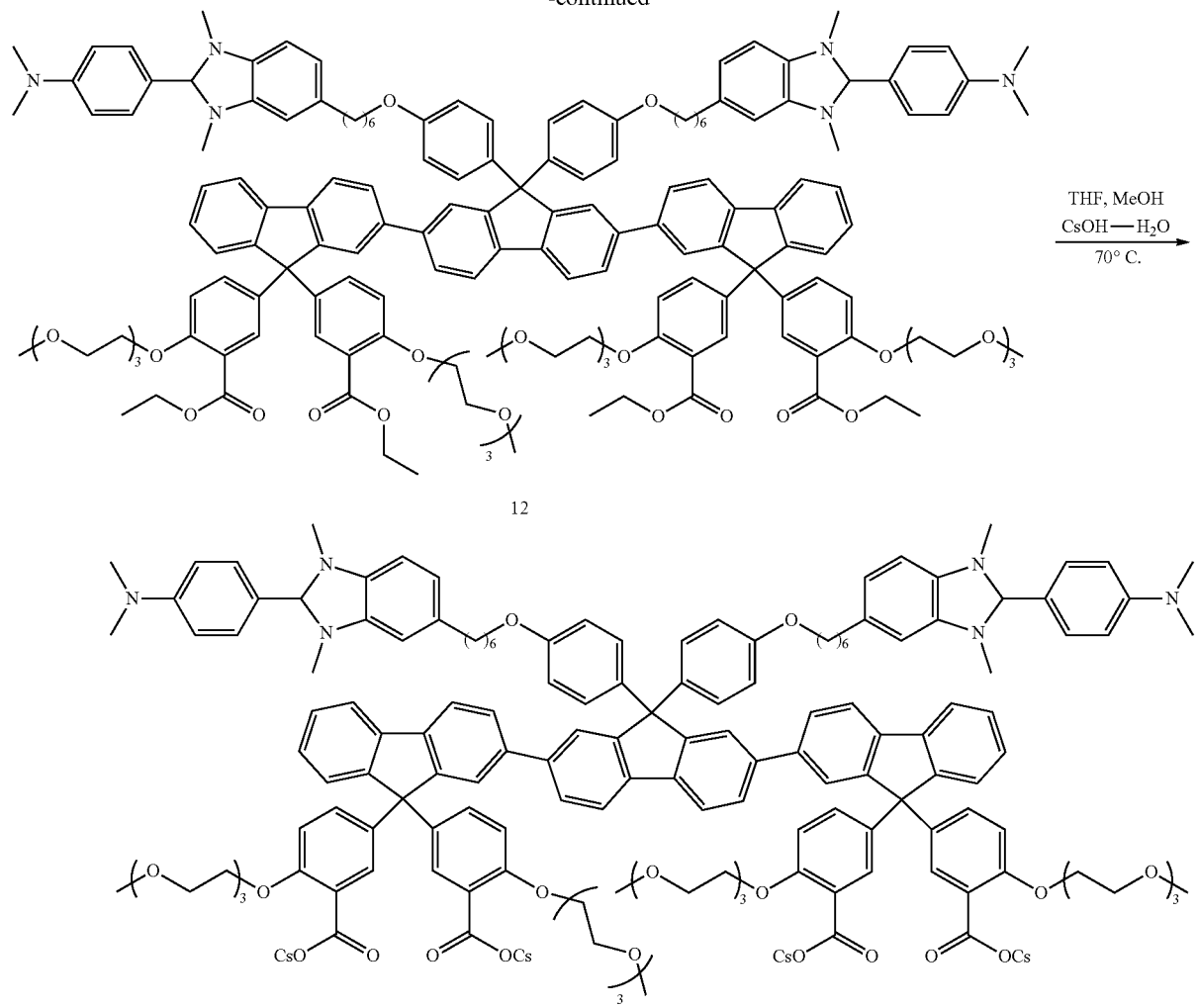

Compound Example 5

Intermediate 9:

Nitrogen was bubbled into a solution of boronic ester 7 (6.4 g, 7.0 mmol) and dibromide 8 (2.5 g, 3.0 mmol) in toluene (60 ml) for 30 minutes. Palladium acetate (2.1 mg, 0.01 mmol), tris(o-methoxyphenyl)phosphine (12.9 mg, 0.04 mmol) and aliquat336 (31.0 mg, 0.08 mmol) were added using degassed toluene (20 ml). Nitrogen was bubbled into the mixture for 30 minutes. Mixture was heated up to 90° C. and a solution of degassed sodium carbonate (15 ml, 10% aqueous, 15.0 mmol) was added. Reaction mixture was stirred over night at 90° C. It was then cooled down to room temperature and a solution of sodium diethyldithiocarbamate trihydrate (1.67 g, 7.4 mmol, in 33 ml water) was added to it. Mixture was stirred for 2 hours at 80° C. and cooled down to room temperature. Phases were separated and organic phase was washed with water (×3) at 40° C., dried over magnesium sulfate and concentrated under reduced pressure. Residue was purified by column chromatography over basic alumina using ethyl acetate as eluent to obtain 6.4 g of Intermediate 9 with 88% HPLC purity, 94% yield.

Intermediate 10:

A solution of Intermediate 9 (6.4 g, 2.87 mmol) in tetrahydrofuran (60 ml) was cooled down to 0° C. Tetrabutyl ammonium fluoride (3.0 g, 11.46 mmol) in solution in tetrahydrofuran (20 ml) was added drop wise. Mixture was stirred for 1.5 hours at 0° C. and water (70 ml) was added to it. Tetrahydrofuran was distillated and residue was extracted with toluene (50 ml), ethyl acetate (20 ml) and dichloromethane (30 ml×2). Combined toluene and ethyl acetate phases were washed with water (×3). Combined dichloromethane phases were washed with water (×3). Combined organic phases were dried over magnesium sulfate and concentrated under reduced pressure. Residue was purified by column chromatography over C18 reversed phase silica using a gradient of acetonitrile to 30% tetrahydrofuran in acetonitrile as eluent. Fractions containing Intermediate 10 were combined, concentrated under reduced pressure, stirred with heptane and filtered to give 2.16 g of Intermediate 10 with 96.9% purity by HPLC, 39% yield.

Intermediate 12:

Nitrogen was bubbled into a mixture of Intermediate 10 (2.16 g, 1.12 mmol), potassium carbonate (0.62 g, 4.50 mmol) and 18-crown-6 (0.059 g, 0.22 mmol) in N,N-dimethylformamide (20 ml) for 30 minutes. Mixture was heated to 70° C. and Intermediate 11 (1.76 g, 3.37 mmol) in solution in degassed N,N-dimethylformamide (20 ml) was added to it. Mixture was stirred for 4 hours at 70° C. whilst nitrogen was bubbling into it. Mixture was cooled down to room temperature, filtered and concentrated under reduced pressure. Residue was dissolved in ethyl acetate, washed with water (×3), dried over magnesium sulfate and concentrated under reduced pressure. Residue was purified by column chromatography over basic alumina using 50% heptane in ethyl acetate followed by 10% methanol in ethyl acetate as eluent. Product was purified by column chromatography over basic alumina using a gradient of ethyl acetate to 10% methanol in ethyl acetate as eluent to obtain 1 g of Intermediate 12, 34% yield.

$^1$H-NMR (400 MHz, CDCl$_3$): δ [ppm] 1.26 (t, 12H), 1.35-1.42 (m, 4H), 1.42-1.49 (m, 4H), 1.56-1.64 (m, 4H), 1.70-1.77 (m, 4H), 2.47-2.54 (m, 16H), 3.0 (s, 12H), 3.34 (s, 12H), 3.51 (m, 8H), 3.59-3.65 (m, 16H), 3.72 (m, 8H), 3.84 (t, 8H), 3.88 (4H), 4.13 (t, 8H), 4.24 (q, 8H), 4.69 (s, 2H), 6.24 (s, 2H), 6.31 (d, J=7.50 Hz, 2H), 6.48 (d, J=7.50 Hz, 2H), 6.74 (d, J=8.38 Hz, 4H), 6.76 (d, J=8.38 Hz, 4H), 6.83, (d, J=8.83 Hz, 4H), 7.17 (d, J=8.83 Hz, 4H), 7.22-7.29 (m, 6H), 7.35 (d, J=6.84 Hz, 4H), 7.41 (d, J=8.39 Hz, 4H), 7.47-7.53 (m, 4H), 7.54 (s, 2H), 7.57 (s, 2H), 7.60 (d, J=1.82 Hz, 4H), 7.75 (d, J=7.76 Hz, 6H).

Compound Example 5

Nitrogen was bubbled in a solution of Intermediate 12 (1.00 g, 0.382 mmol) and tetrahydrofuran (5 ml) for 5 minutes. A solution of cesium hydroxide monohydrate (0.769 g 4.581 mmol) in water (1 ml) and methanol (2 ml) was added to it. Nitrogen was bubbled in the mixture for 10 minutes after which the mixture was heated to 70° C. for 16 hours. Once cooled, the mixture was evaporated to dryness under reduced pressure. The residue was triturated with water (30 ml) under a constant flow of nitrogen. Degassed acetonitrile (50 ml) was added to the residue and the mixture was evaporated to dryness. The residue was dried in a vacuum oven at 50° C. for 16 hours to afford Compound Example 5 as a white solid, 0.370 g, 95% pure by NMR, 32% yield.

$^1$H-NMR (600 MHz, MeOH-D$_4$): δ$_H$ [ppm] 1.31-1.36 (m, 4H), 1.40-1.45 (m, 4H), 1.57-1.59 (m, 4H), 1.64-1.70 (m, 4H), 2.39 (s, 6H), 2.40 (s, 6H), 2.46 (t, J=7.5 Hz, 4H), 2.92 (s, 12H), 3.26 (s, 12H), 3.46 (m, 8H), 3.51-3.57 (m, 16H), 3.60 (m, 8H), 3.74 (m, 8H), 3.82 (t, J=6.2 Hz, 4H), 4.05-4.12 (m, 8H), 4.49 (s, 2H), 6.23-6.29 (m, 3H), 6.42 (d, J=7.7 Hz, 2H), 6.72-6.78 (m, 7H), 6.82-6.86 (m, 4H), 7.08-7.12 (m, 8H), 7.19-7.23 (m, 6H), 7.29-7.35 (m, 5H), 7.40 (d, J=7.5 Hz, 2H), 7.46 (d, J=7.6 Hz, 2H), 7.49-7.56 (m, 6H), 7.74 (d, J=7.5 Hz, 4H), 7.80 (d, J=7.3 Hz, 2H).

Compound Example 6

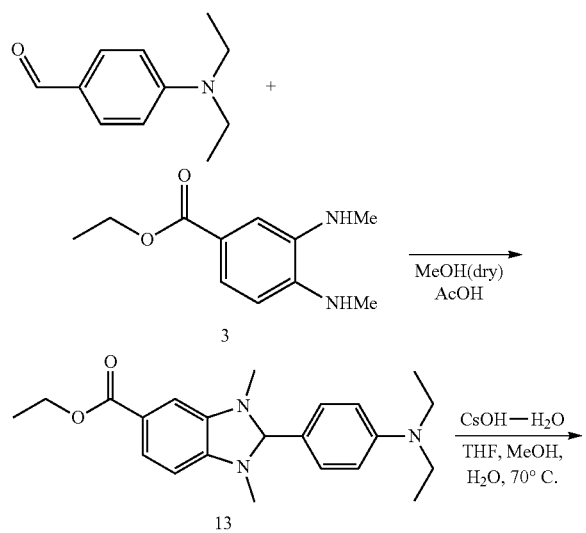

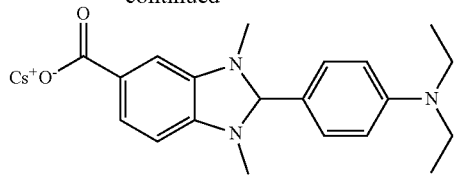

Compound Example 6

Intermediate 13

Nitrogen was bubbled in a suspension of Intermediate 3 (1.00 g, 4.802 mmol) and 4-diethylaminobenzaldehyde (0.85 g, 4.802 mmol) in anhydrous methanol (3 ml) for 10 minutes. Acetic acid (0.1 ml) was added and nitrogen was bubbled into the reaction mixture for 5 minutes. The reaction was stirred for 5 hours at room temperature then cooled to 0° C. using and degassed methanol (4 ml) was added. The mixture was stirred for 5 minutes and was filtered. The solid was washed with cold methanol (20 ml) and dried in a vacuum oven at 50° C. for 16 hours to afford Intermediate 13 as an off-white solid, 1.30 g, 99% pure by NMR, 74% yield.

$^1$H-NMR (600 MHz, CDCl$_3$): δ$_H$ [ppm] 1.18 (t, J=7.0 Hz, 6H), 1.36 (t, J=7.1 Hz, 3H), 2.59 (s, 6H), 3.37 (q, J=7.1 Hz, 4H), 4.29-4.34 (m, 2H), 5.08 (s, 1H), 6.28 (2, J=7.9 Hz, 1H), 6.66-6.69 (m, 2H), 6.95 (d, J=2.0 Hz, 2H), 7.29-7.32 (m, 2H), 7.50 (dd, J=7.5 Hz, J=1.5 Hz, 1H).

Compound Example 6

Nitrogen was bubbled in a mixture of Intermediate 13 (1-200 g, 3.268 mmol) and tertrahydrofuran (5 ml) for 5 minutes. A solution of cesium hydroxide monohydrate (1.646 g, 9.803 mmol) in water (1 ml) and methanol (2 ml). Nitrogen was bubbled in the mixture for 10 minutes and the mixture was heated to 70° C. for 16 hours. Once cooled, the mixture was evaporated to dryness under reduced pressure. The residue was dissolved in water and purified by column chromatography over C18 reversed phase silica using a gradient of water to water:methanol 1:1. The combined fractions containing Compound Example 6 were evaporated to dryness under reduced pressure. The residue was triturated with acetonitrile (20 ml), filtered and dried in a vacuum oven for 16 hours at 50° C. to afford 1.154 g of Compound Example 6 as a white powder at 99% purity by NMR, 75% yield.

$^1$H-NMR (600 MHz, MeOH-D$_4$): δ$_H$ [ppm] 1.16 (t, J=6.8 Hz, 6H), 2.53 (s, 3H), 2.54 (s, 3H), 3.40 (q, J=7.4 Hz, 4H), 4.74 (s, 1H), 6.34 (d, J=8.0 Hz, 1H), 6.71-6.74 (m, 2H), 6.04 (d, J=1.5 Hz, 1H), 7.32-7.34 (m, 2H), 7.41 (dd, J=8.0 Hz, J=1.5 Hz, 1H).

Compound Example 7

The Cs+ cation of Compound Example 1 was exchanged for a Li+ cation to give Compound Example 7:

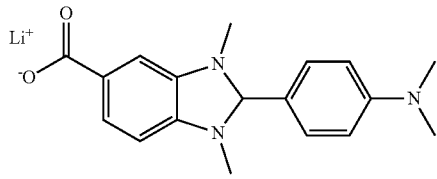

Formulation Examples

Formulations were formed by dissolving Compound Example 1 and Acceptor Polymer 1 in methanol solvent to form solutions of 0.4 wt % concentration of the Acceptor Polymer 1/Compound Example 1 composition.

Formulations with Acceptor Polymer 1:Compound Example 1 weight ratios of 90:10, 80:20, 70:30, 60:40 and 50:50 were formed.

Acceptor Polymer 1 has the following structure:

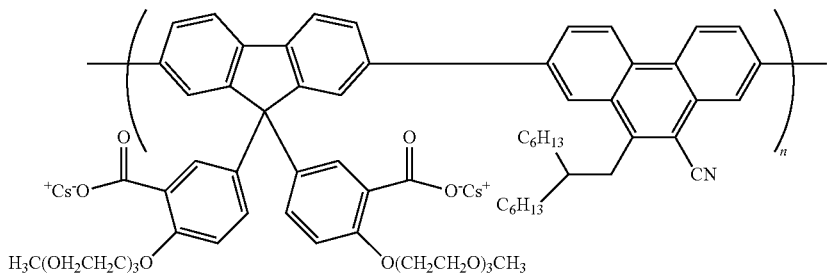

Acceptor Polymer 1 was formed by Suzuki polymerization as disclosed in WO00/53656 of 50 mol % each of the following monomers to form a precursor polymer followed by hydrolysis of the precursor polymer:

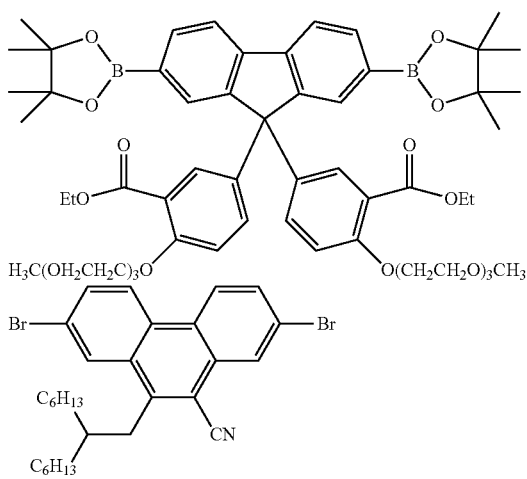

To hydrolyse the polymer, nitrogen was bubbled for 30 minutes in 113 ml of tetrahydrofuran, in 42 ml of methanol and in a solution of cesium hydroxide monohydrate (0.80 g, 4.73 mmol) in 3.4 ml of water. 2.24 g of the precursor polymer was suspended in the tetrahydrofuran and heated up to 65° C. Mixture was stirred until full dissolution of the polymer. Methanol was added drop wise followed by the cesium hydroxide solution. Mixture was stirred at 65° C. for 16 hours and cooled down to room temperature. Solution was filtered and concentrated to 42 ml. It was precipitated into 800 ml of diethyl ether. Slurry was stirred for 10 minutes and filtered. Polymer was dried in vacuum oven at 50° C. overnight to yield 2.52 g of Acceptor Polymer 1, 96% yield.

Device Example 1

Green phosphorescent devices having the following structure were prepared:
ITO/HIL (50 nm)/LEL (80 nm)/EIL (20 nm)/Ag (100 nm)
in which ITO is an indium tin oxide anode; HIL is a hole-injection layer; EIL is an electron injection layer and LEL is a light-emitting layer.

To form the devices, a substrate carrying ITO was cleaned using UV/Ozone. The hole injection layer was formed by spin-coating an aqueous formulation of a hole-injection material available from Nissan Chemical Industries and heating the resultant layer. The light-emitting layer was formed by spin-coating Host Polymer 1 and Green Phosphorescent Emitter 1 with a light-emitting dopant from xylene solution in a glove box. The electron-injection layer was formed by spin-coating a formulation of Acceptor Polymer 1 and Compound Example 1 from methanol solution in a ratio as given in Table 1. The cathode was formed by evaporation of silver.

After spin-coating the electron injection layer, the EIL was dried at 80° C. for 10 min, in a glovebox, followed by deposition of the cathode by thermal evaporation in vacuum.

The devices were then encapsulated and heated at 80° C. for 10 minutes.

TABLE 1

| Device | Acceptor Polymer 1:Compound Example 1 wt:wt |
|---|---|
| Device Example 1A | 90:10 |
| Device Example 1B | 80:20 |
| Device Example 1C | 60:40 |

Host Polymer 1 is a block copolymer formed by Suzuki polymerization as described in WO 00/53656 of the following monomers:

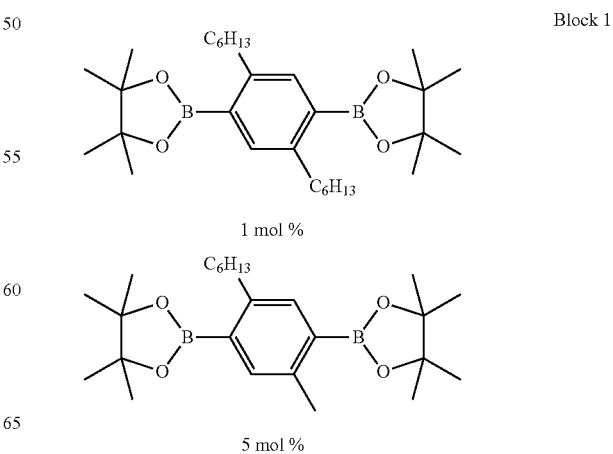

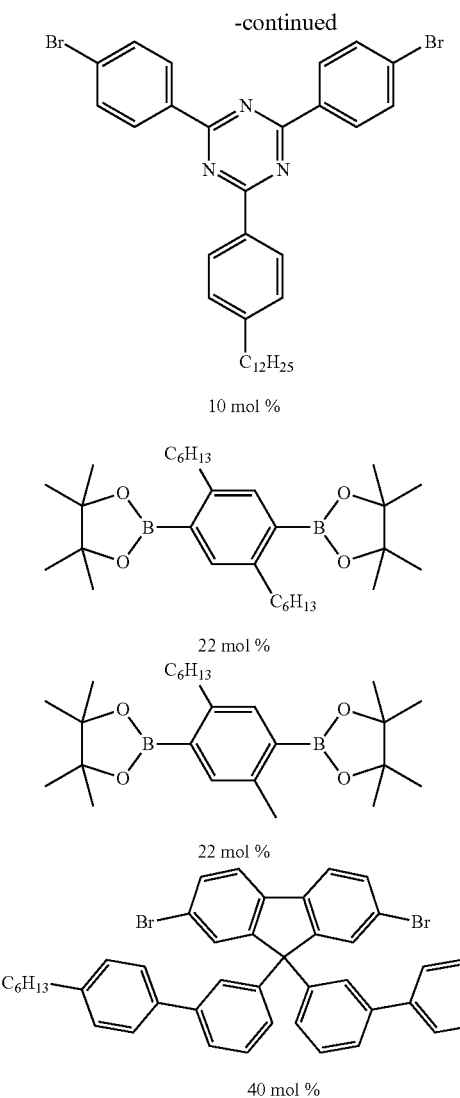

10 mol %

Block 2

22 mol %

22 mol %

40 mol %

Green Phosphorescent Emitter 1 has the following structure:

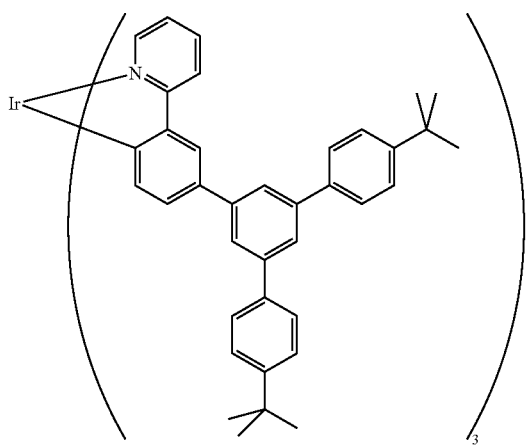

Figure 2:
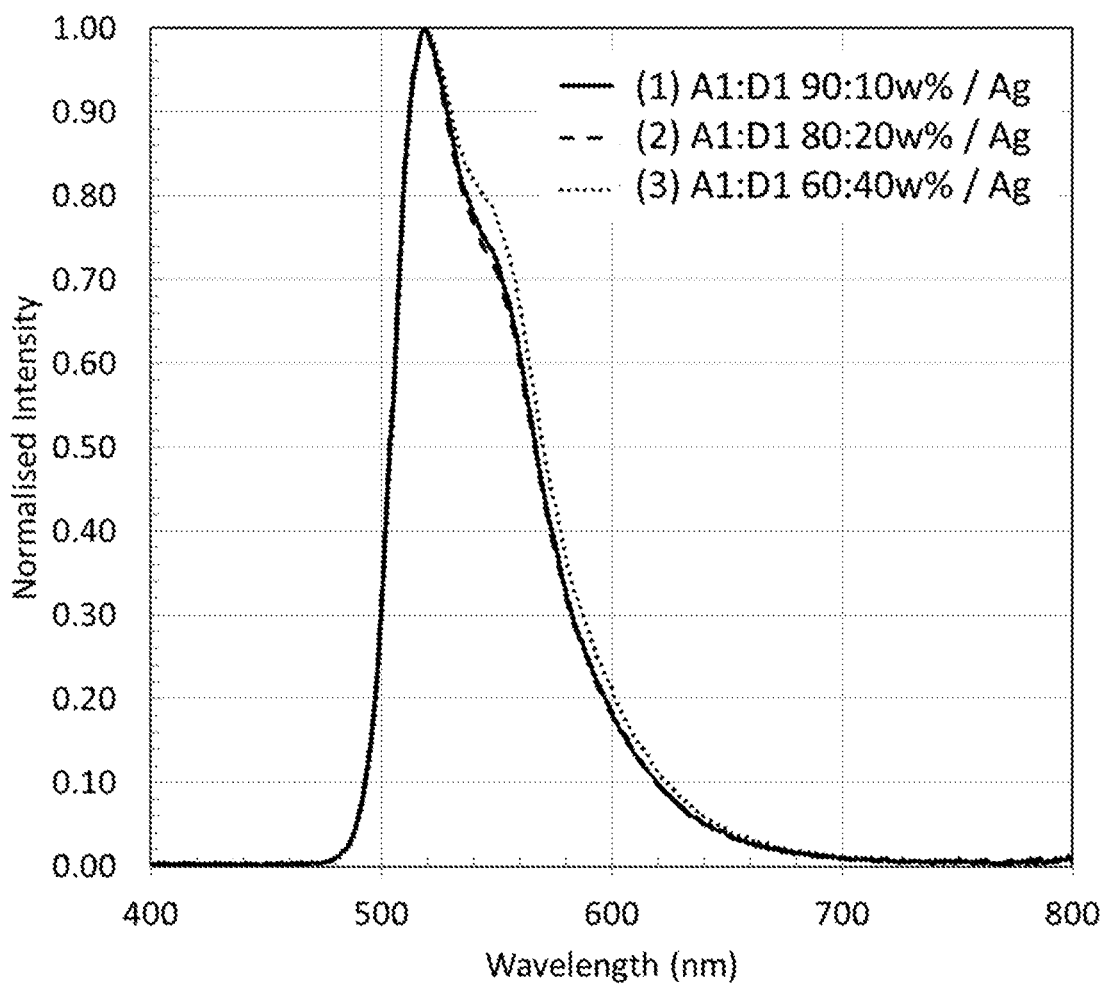
FIG. 2 shows the electroluminescent spectra for green light emitting OLEDs according to embodiments of the invention.
Figure 3:
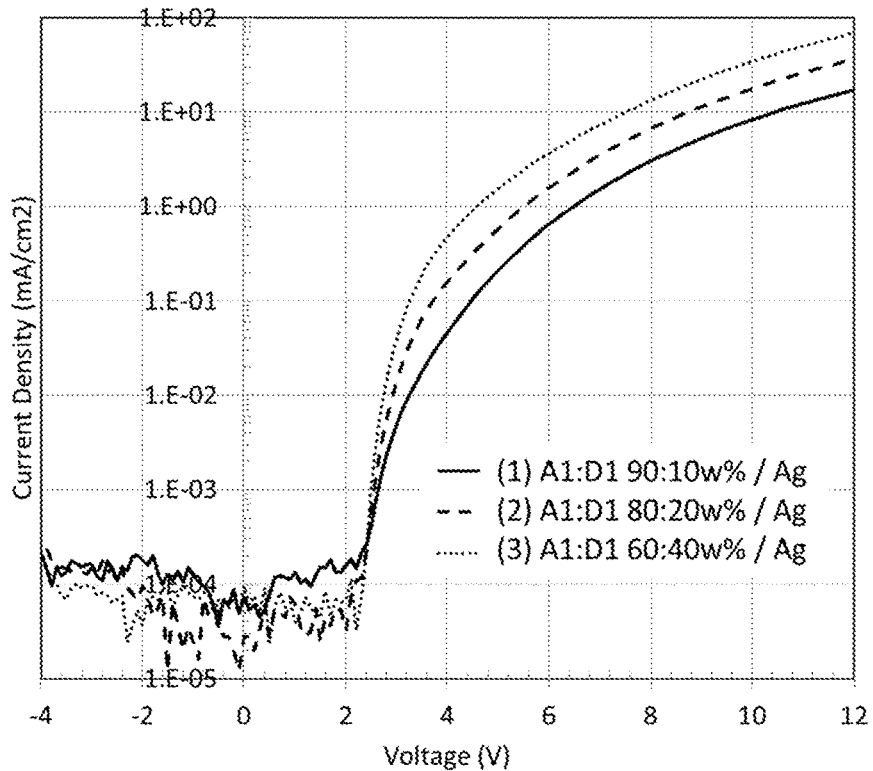
FIG. 3 is a graph of current density vs. voltage for green light emitting OLEDs according to embodiments of the invention.
Figure 4:
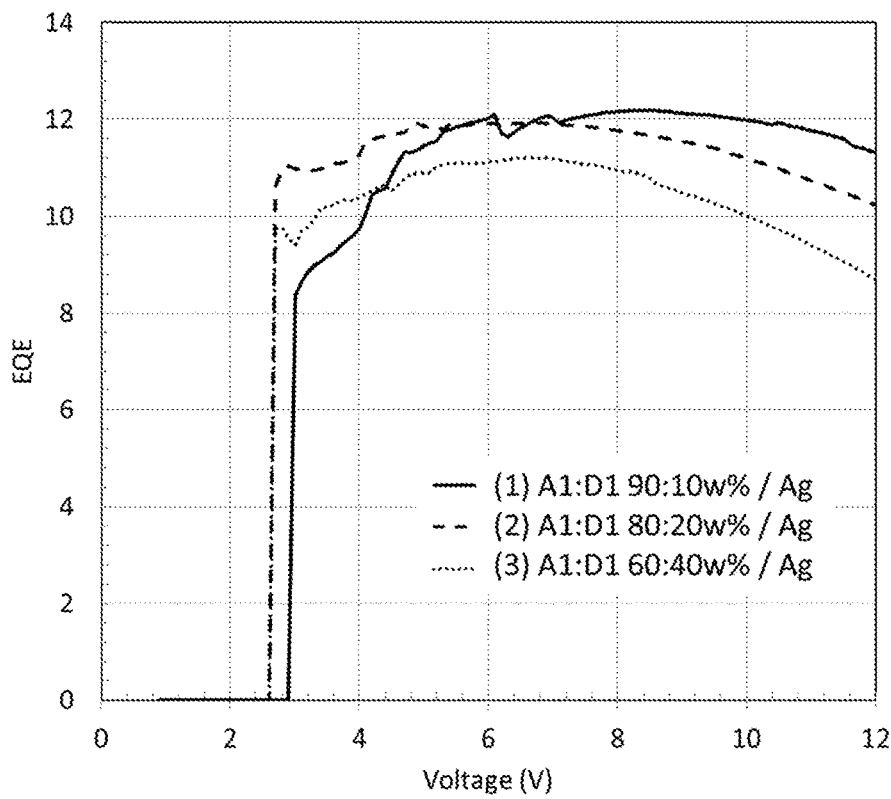
FIG. 4 is a graph of external quantum efficiency vs. voltage for green light emitting OLEDs according to embodiments of the invention.
Figure 5:
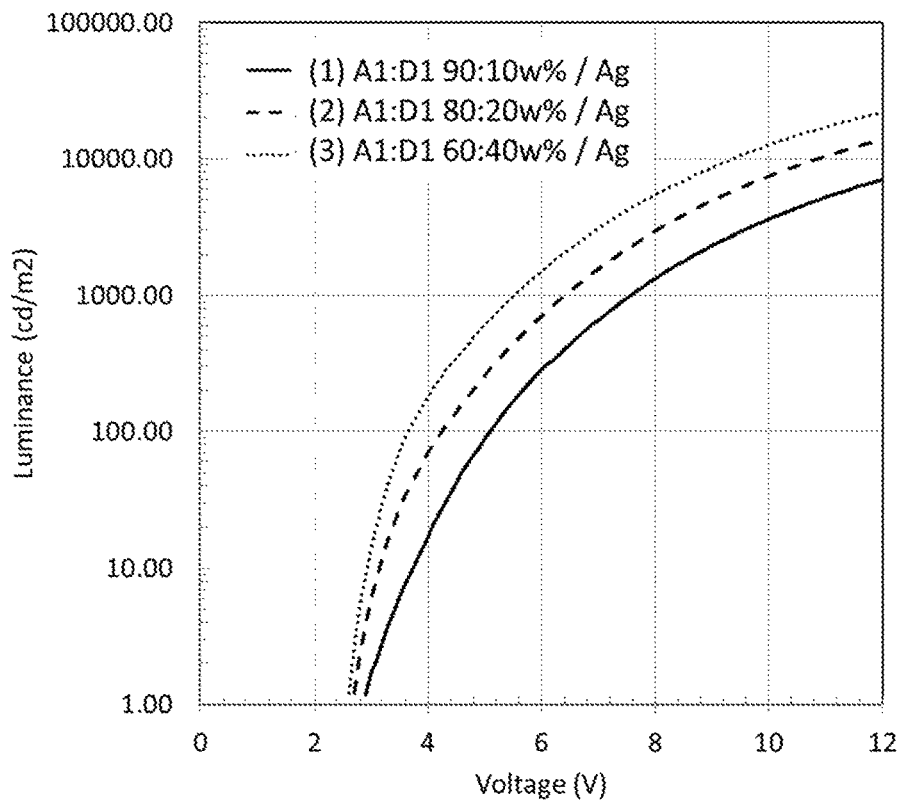
FIG. 5 is a graph of luminance vs. voltage for green light emitting OLEDs according to embodiments of the invention.
Figure 6:
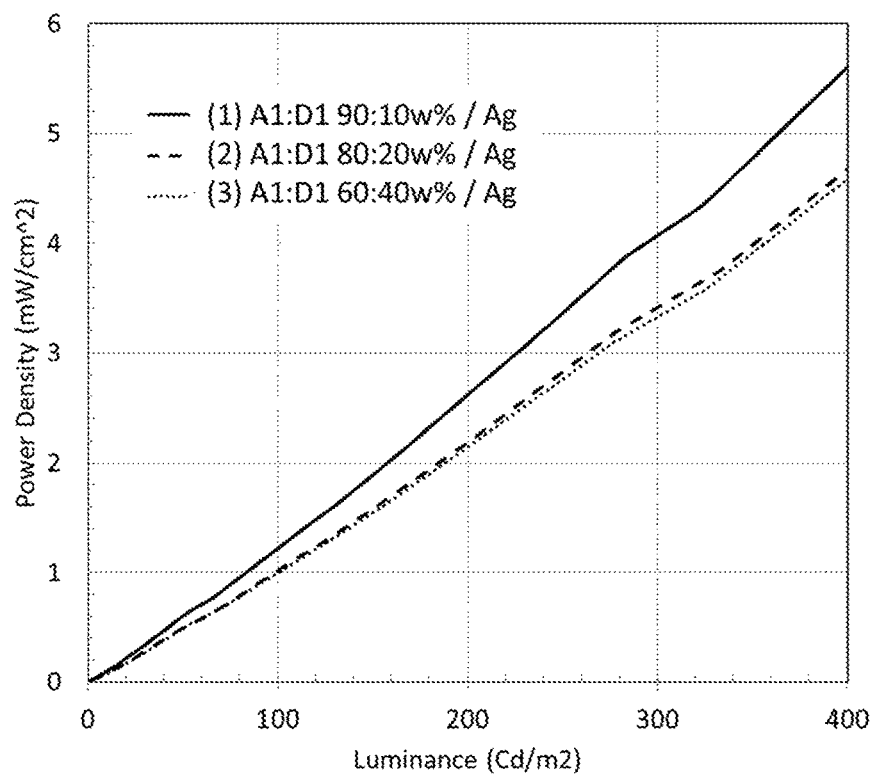
FIG. 6 is a graph of power density vs. luminance for green light emitting OLEDs according to embodiments of the invention.

With reference to FIG. 2 of the figures, in which dopant Compound Example 1 is denoted "D1" and Acceptor Polymer 1 is denoted "A1", the n-dopant concentration has very little effect on the colour of emission of the device.

With reference to FIG. 3-6, increasing the concentration of n-dopant results in an increase in device conductivity, indicating a higher degree of n-doping at higher n-dopant concentrations.

Device Example 2

White light-emitting devices having the following structure were prepared:

ITO/HIL (35 nm)/HTL (22 nm)/LEL (65 nm)/EIL (20 nm)/ Ag (100 nm)

in which ITO is an indium tin oxide anode; HIL is a hole-injection layer; HTL is a hole-transporting layer; LEL is a light-emitting layer; and EIL is an electron injection layer.

The devices were formed as described for Device Example 1 except that a hole transporting layer was formed between HIL and LEL by spin-coating Hole-Transporting Polymer 1 from xylene solution and crosslinking the polymer by heating, and LEL was formed by spin-coating White Polymer 1 from xylene solution.

The Acceptor Polymer 1:Compound Example 1 weight ratio was as given in Table 2. The cathode was formed by evaporation of silver.

TABLE 2

| Device | Acceptor Polymer 1:Compound Example 1 wt:wt |
| --- | --- |
| Comparative Device 2A | 100:0 |
| Device Example 2A | 70:30 |
| Device Example 2B | 50:50 |

For the purpose of comparison, Comparative Device 2 was formed as described above except that no electron-injection layer was formed and the silver cathode was formed directly on the light-emitting layer.

Hole-Transporting Polymer 1 was formed by Suzuki polymerization as described in WO 00/53656 of 1,4-dialkylphenylene repeat units of formula, an amine repeat unit as described in and 2,7-linked fluorene repeat units substituted with crosslinkable groups.

White Polymer 1 was formed by Suzuki polymerization as described in WO 00/53656 of the following monomers:

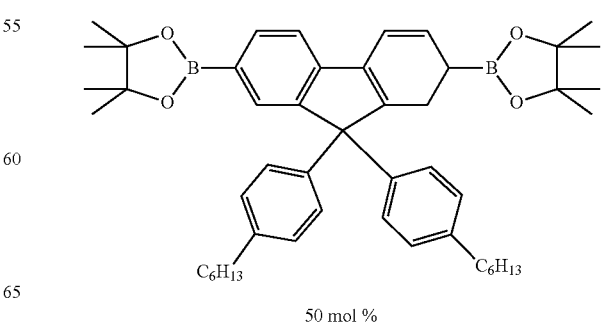

50 mol %

-continued

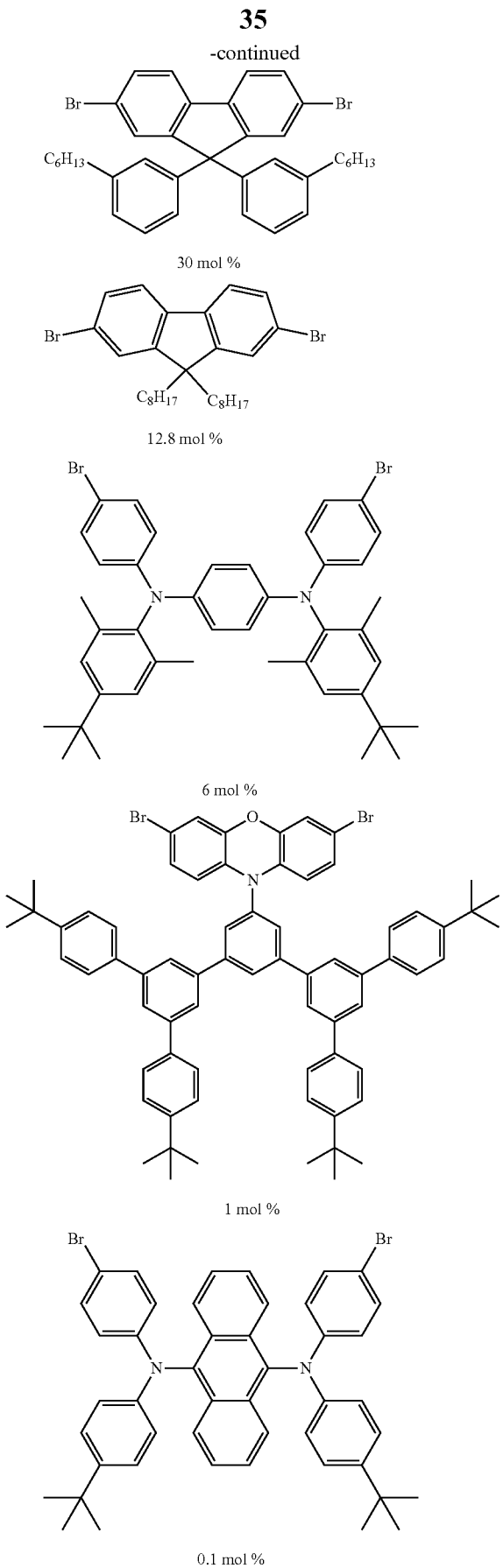

30 mol %

12.8 mol %

6 mol %

1 mol %

0.1 mol %

-continued

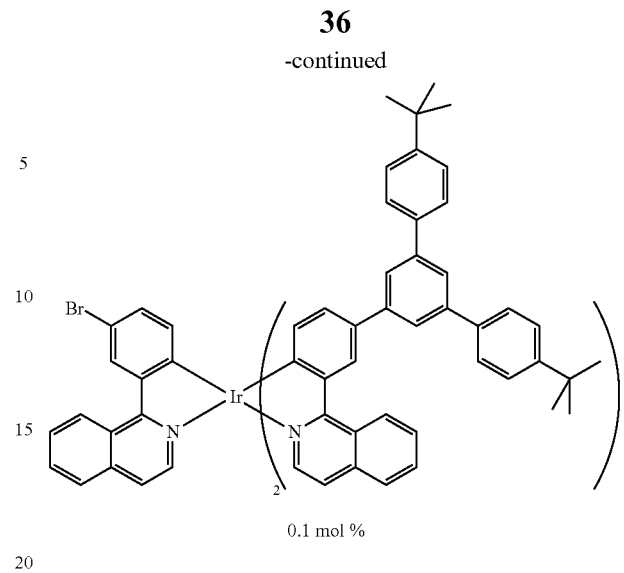

0.1 mol %

Figure 7:
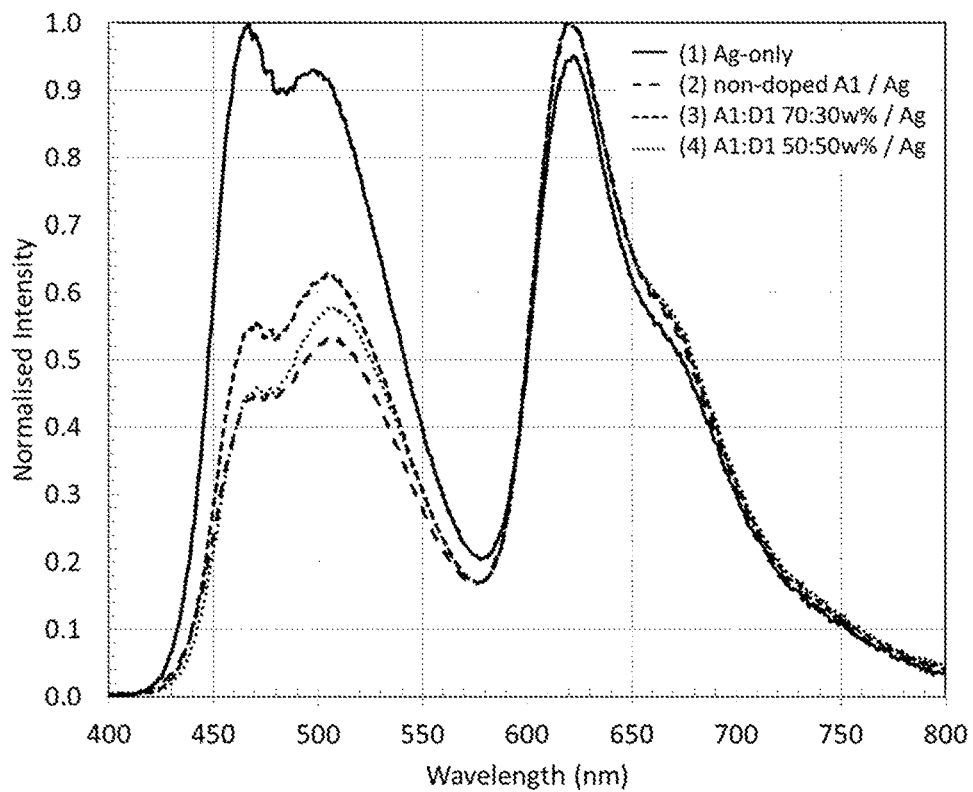
FIG. 7 shows the electroluminescent spectra for white light emitting OLEDs according to embodiments of the invention and comparative white OLEDs.

With reference to FIG. 7, the emission of Comparative Device 2 is very different from those of Device Examples 2A and 2B, indicating an effect on charge (hole and electron) balance in the light-emitting layer.

Figure 8:
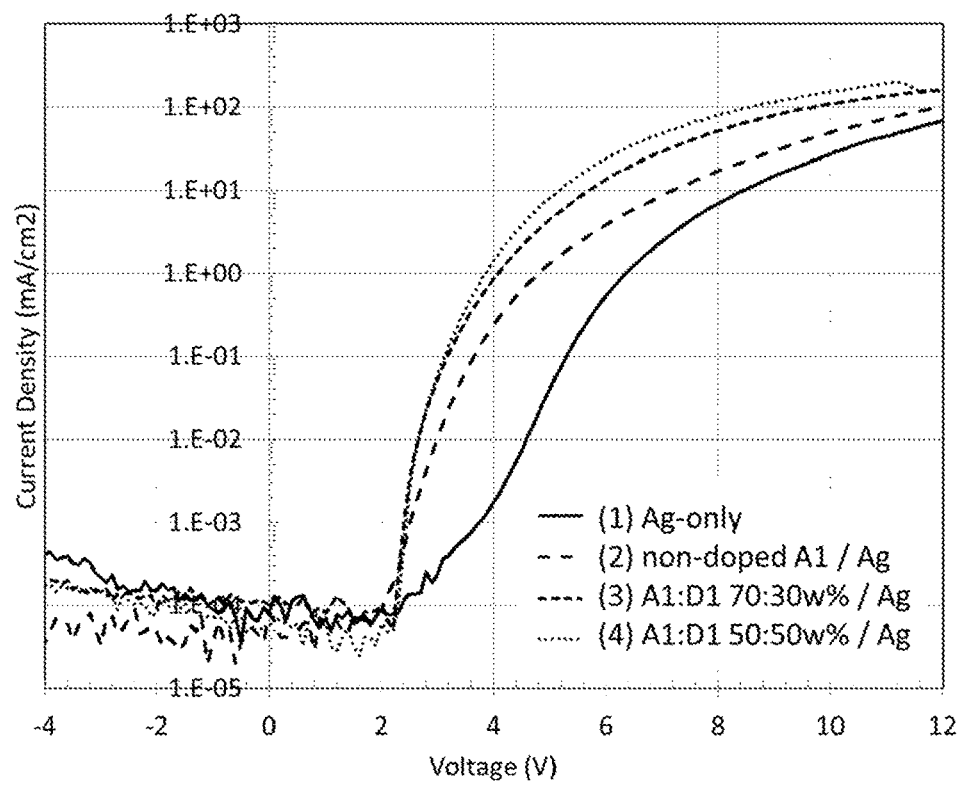
FIG. 8 is a graph of current density vs. voltage for white light emitting OLEDs according to embodiments of the invention and comparative white devices.
Figure 9:
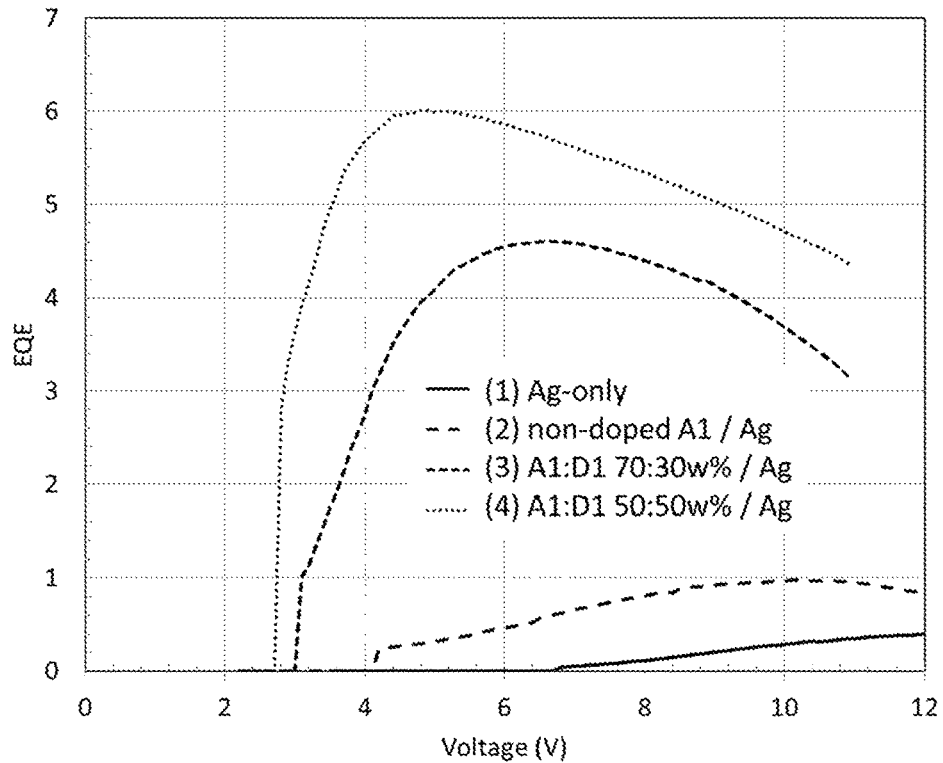
FIG. 9 is a graph of external quantum efficiency vs. voltage for white light emitting OLEDs according to embodiments of the invention and comparative white OLEDs.
Figure 10:
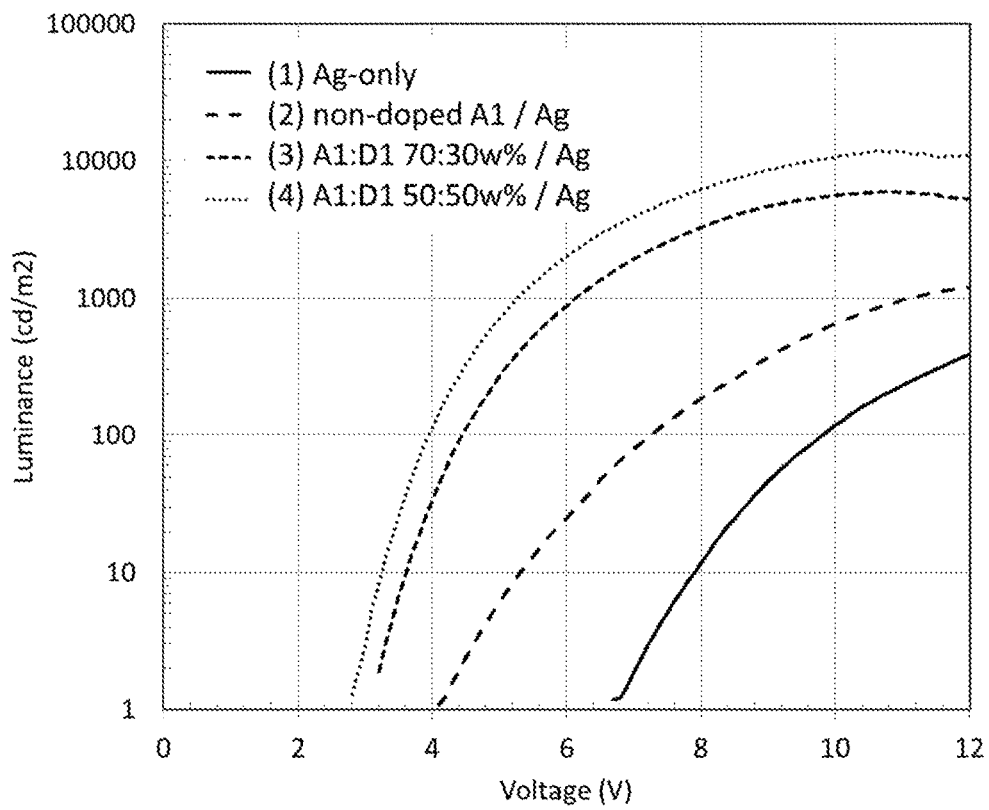
FIG. 10 is a graph of luminance vs. voltage for white light emitting OLEDs according to embodiments of the invention and comparative white OLEDs.
Figure 11:
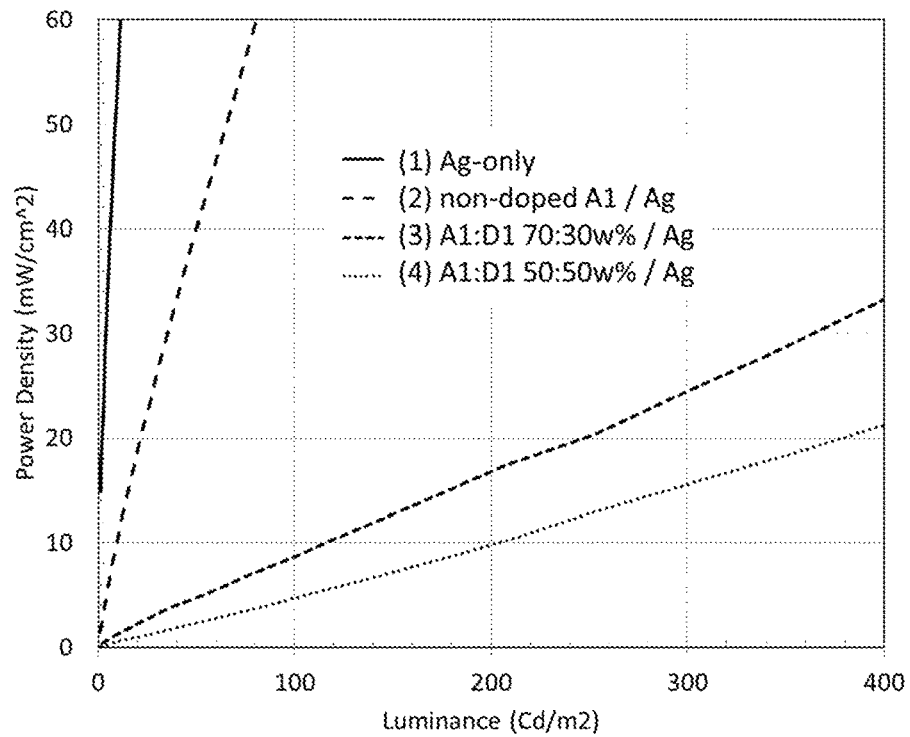
FIG. 11 is a graph of power density vs. luminance for white light emitting OLEDs according to embodiments of the invention and comparative white OLEDs.

With reference to FIGS. 8-10, Device Examples 2A and 2B give higher current density, external quantum efficiency and luminance at a given voltage than either Comparative Device 2 or 2A. With reference to FIG. 11, increasing dopant concentration reduces the power density required for achieving a given luminance.

Device Example 3

Blue light-emitting devices were formed as described for Device Example 2 except LEL was formed by spin-coating Blue Polymer 1 from xylene solution.

The Acceptor Polymer 1:Compound Example 1 weight ratio was as given in Table 3. The cathode was formed by evaporation of silver.

TABLE 3

| Device | Acceptor Polymer 1:Compound Example 1 wt:wt |
|---|---|
| Comparative Device 3 | 100:0 |
| Device Example 3A | 70:30 |
| Device Example 3B | 60:40 |
| Device Example 3C | 50:50 |

For the purpose of comparison, Comparative Device 3 was formed as described above except that no electron-injection layer was formed and the silver cathode was formed directly on the light-emitting layer.

Blue Polymer 1 is a blue fluorescent polymer comprising 2,7-linked fluorene repeat units and an amine repeat unit having the following structure formed by Suzuki polymerization as described in WO 00/53656:

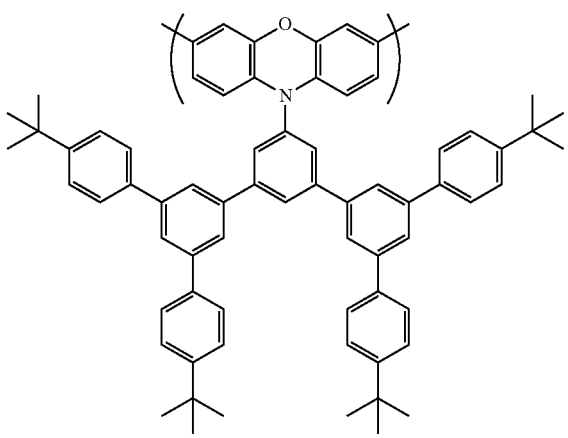

Figure 12:
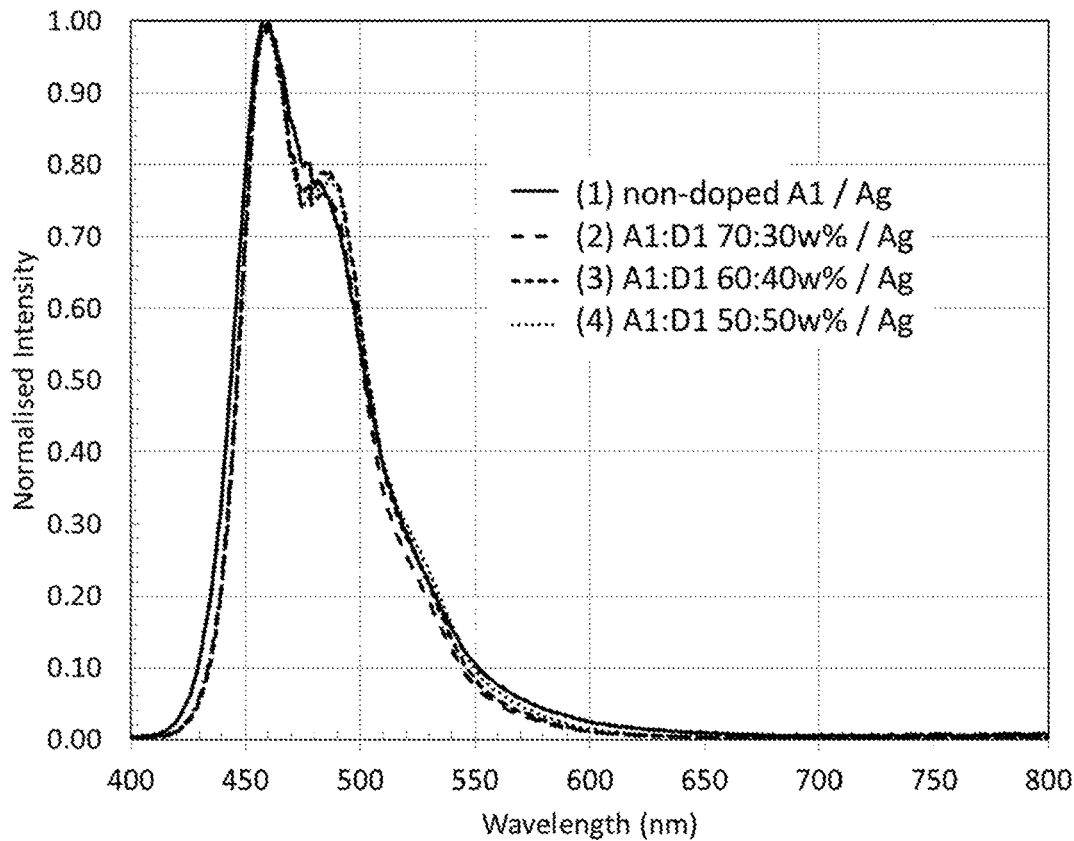
FIG. 12 shows the electroluminescent spectra for blue light emitting OLEDs according to embodiments of the invention and a comparative blue OLED.

With reference to FIG. 12, no light was observed from Comparative Device 3. Very similar spectra were obtained for all other devices.

Figure 13:
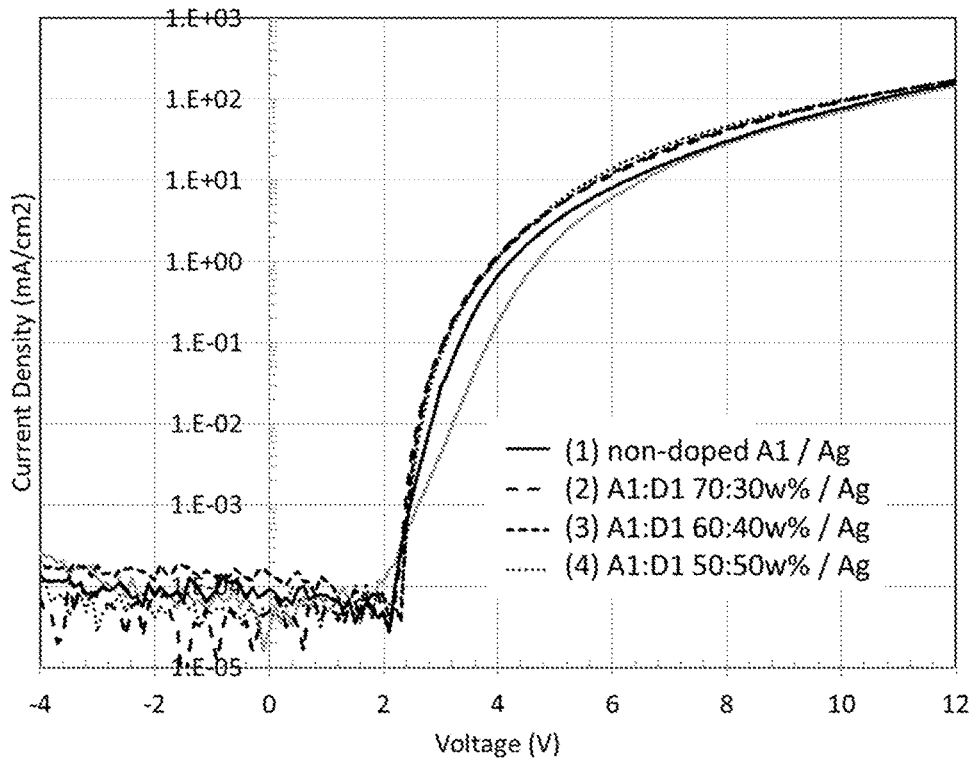
FIG. 13 is a graph of current density vs. voltage for blue light emitting OLEDs according to embodiments of the invention and a comparative blue OLED.
Figure 14:
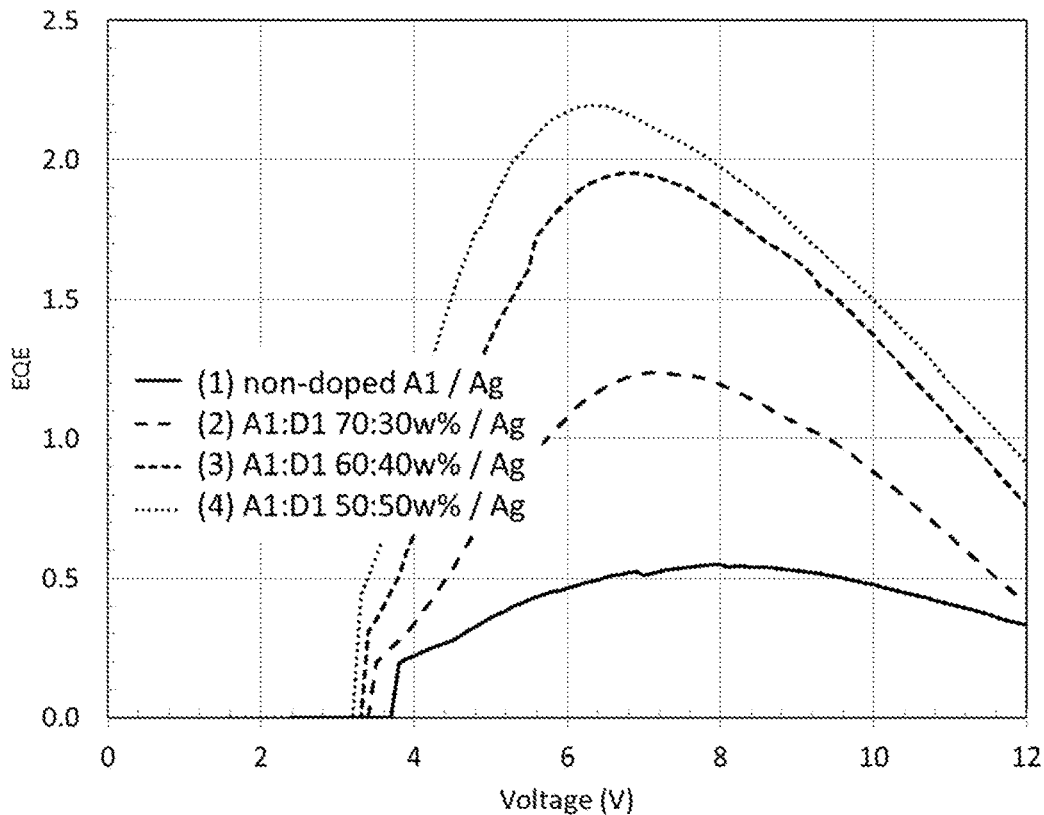
FIG. 14 is a graph of external quantum efficiency vs. voltage for blue light emitting OLEDs according to embodiments of the invention and a comparative blue OLED.
Figure 15:
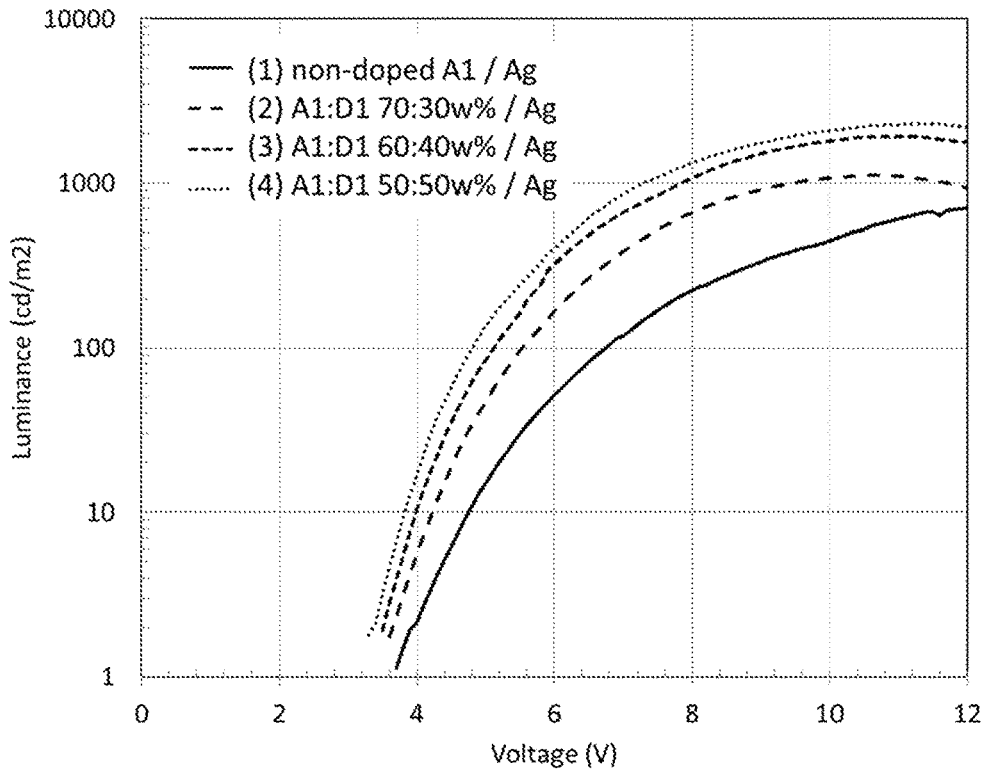
FIG. 15 is a graph of luminance vs. voltage for blue light emitting OLEDs according to embodiments of the invention and a comparative blue OLED.

With reference to FIGS. 13-15 current density, external quantum efficiency and luminance are higher at a given voltage for the exemplary devices than for the comparative devices.

Figure 16:
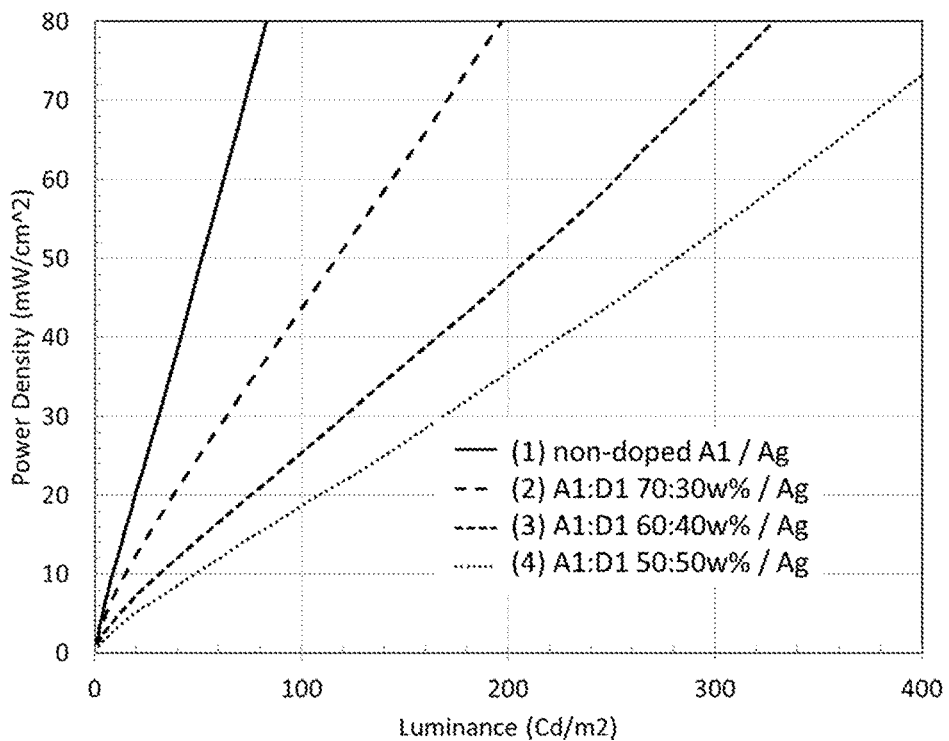
FIG. 16 is a graph of power density vs. luminance for blue light emitting OLEDs according to embodiments of the invention and a comparative blue OLED.

With reference to FIG. 16, increasing dopant concentration reduces the power density at a given luminance.

Device Example 4

A device having the following structure was prepared:
ITO/HIL (50 nm)/LEL (80 nm)/EIL (20 nm)/Ag (100 nm)

The device was formed according to the process described above.

The light-emitting layer was formed by spin-coating a composition of Host Polymer 1, and Green Phosphorescent Emitter 1, described above, from xylene solution.

The EIL was formed by spin-coating a composition of Acceptor Polymer 1, described above (80 wt %), and NADH (20 wt %) from methanol solution:

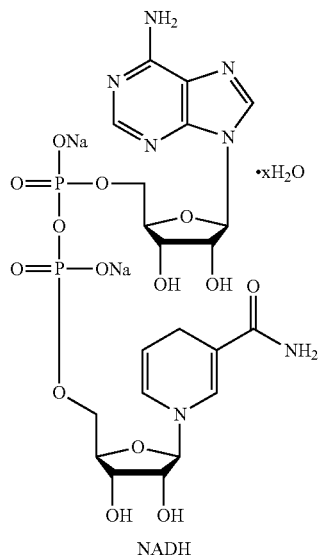

NADH

Comparative Device 4A was formed as for Device Example 4 except that no electron injection layer was formed.

Comparative Device 4B was formed as for Device Example 4 except that no NADH was included in the electron injection layer.

Figure 17:
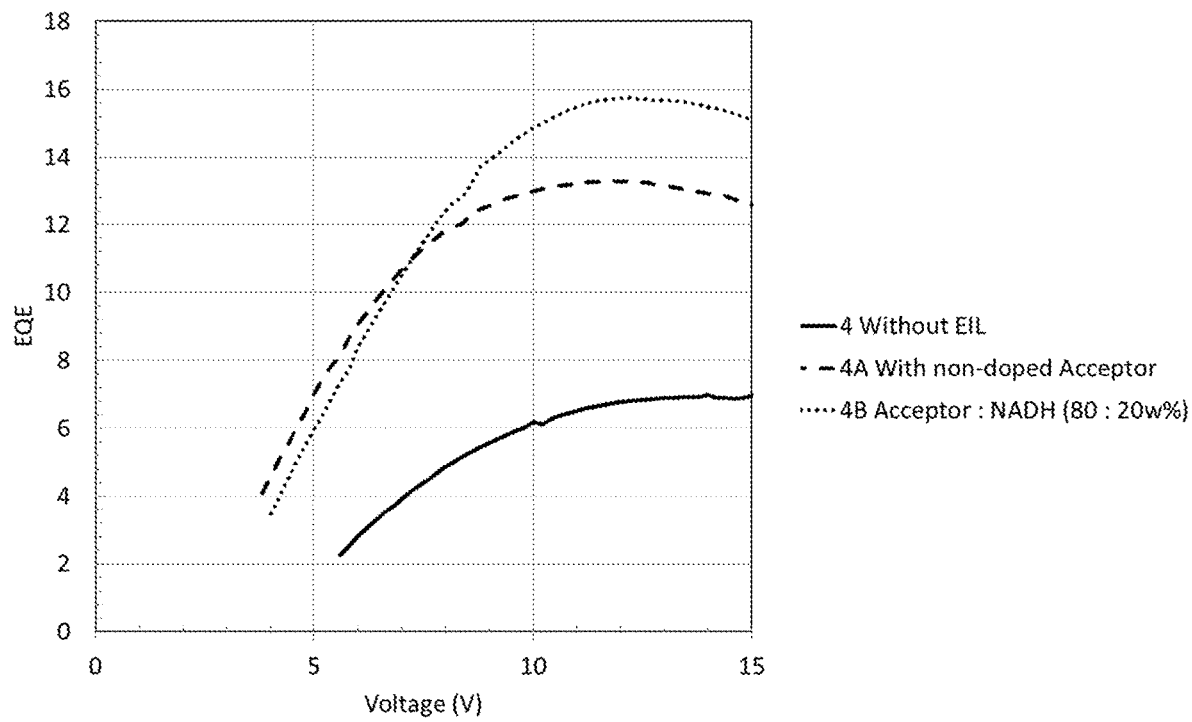
FIG. 17 is a graph of external quantum efficiency vs. voltage for a green phosphorescent OLED according to an embodiment of the invention and comparative OLEDs.

With reference to FIG. 17, Comparative Device 4A (solid line in FIG. 17), which contains no electron injection layer, has a much lower external quantum efficiency than for either Comparative Device 4B (dashed line) or Device Example 4 (dotted line), and Device Example 4 has a similar EQE at lower voltages and a significantly higher EQE at higher voltages as compared to Comparative Device 4B. A higher peak efficiency is achieved by Device Example 4 than either Comparative Device 4A or 4B.

Device Example 5A

A blue light-emitting OLED was prepared as described in Device Example 3 except that the electron-injection layer was formed to a thickness of 5 nm by spin-coating Compound Example 1 (30 wt %) and Acceptor Polymer 1 (70 wt %).

Device Example 5B

Figure 18:
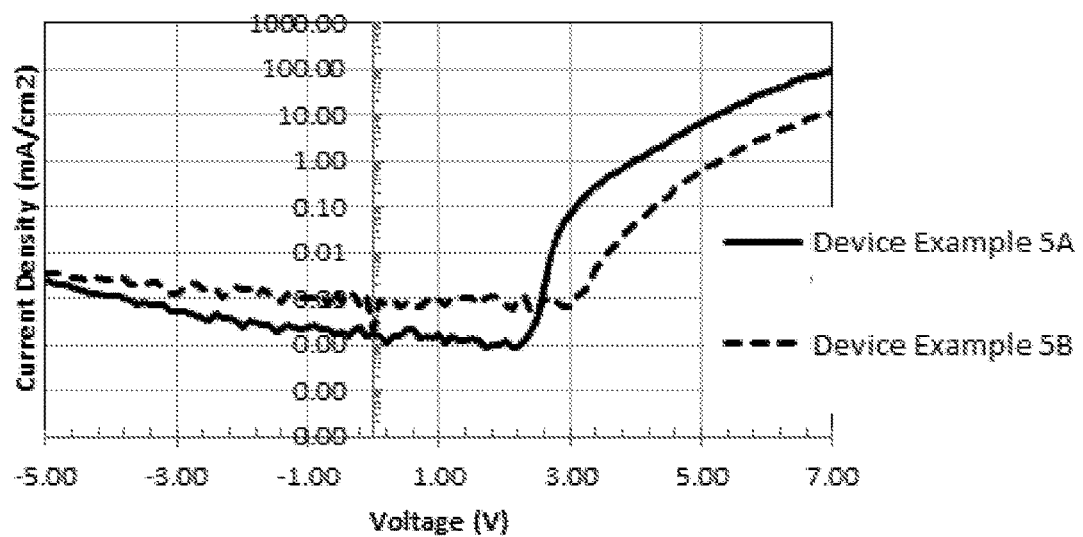
FIG. 18 is a graph of current density vs. voltage for blue light emitting OLEDs containing Compound Example 1 or Compound Example 4.

A device was prepared as described for Device Example 5A except that Compound Example 4 was used in place of Compound Example 1. With reference to FIG. 18, the current density of Device Example 5A is significantly higher than that of Device Example 5B. Without wishing to be bound by any theory, the distance between the ionic group and the benzimidazole group of the compound of formula (I) may affect the n-doping strength of the dopant.

Device Examples 6A-6C

A device having the following structure was prepared:
ITO/HBL (10 nm)/LEL (100 nm)/EIL (10 nm)/Ag (100 nm)
in which ITO is an indium tin oxide anode; HBL is a hole-blocking layer; EIL is an electron injection layer and LEL is a light-emitting layer.

Electron current dominates due to the presence of the hole-blocking layer between the anode and the light-emitting layer.

To form the devices, a substrate carrying ITO was cleaned using UV/Ozone. The hole-blocking layer was formed by spin-coating Hole Blocking Polymer 1, illustrated below, and heating the resultant layer. The light-emitting layer was formed by spin-coating Blue Polymer 1 from xylene solution in a glove box. The electron-injection layer was formed by spin-coating a formulation of Acceptor Polymer 1 and a compound as set out in Table 4 followed by drying at 80° C. for 10 min_in a glovebox. The cathode was formed by evaporation of silver.

The devices were then encapsulated and heated at 80° C. for 10 minutes.

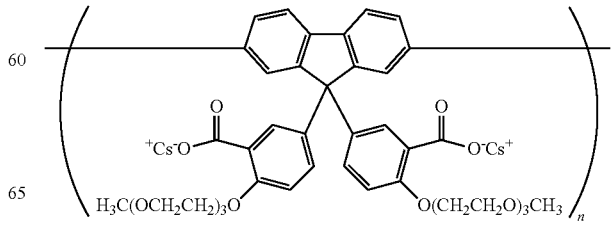

Hole-Blocking Polymer 1

TABLE 4

| Device Example | Compound |
|---|---|
| 6A | Compound Example 1 |
| 6B | Compound Example 7 |
| 6C | Compound Example 2 |

Figure 19:
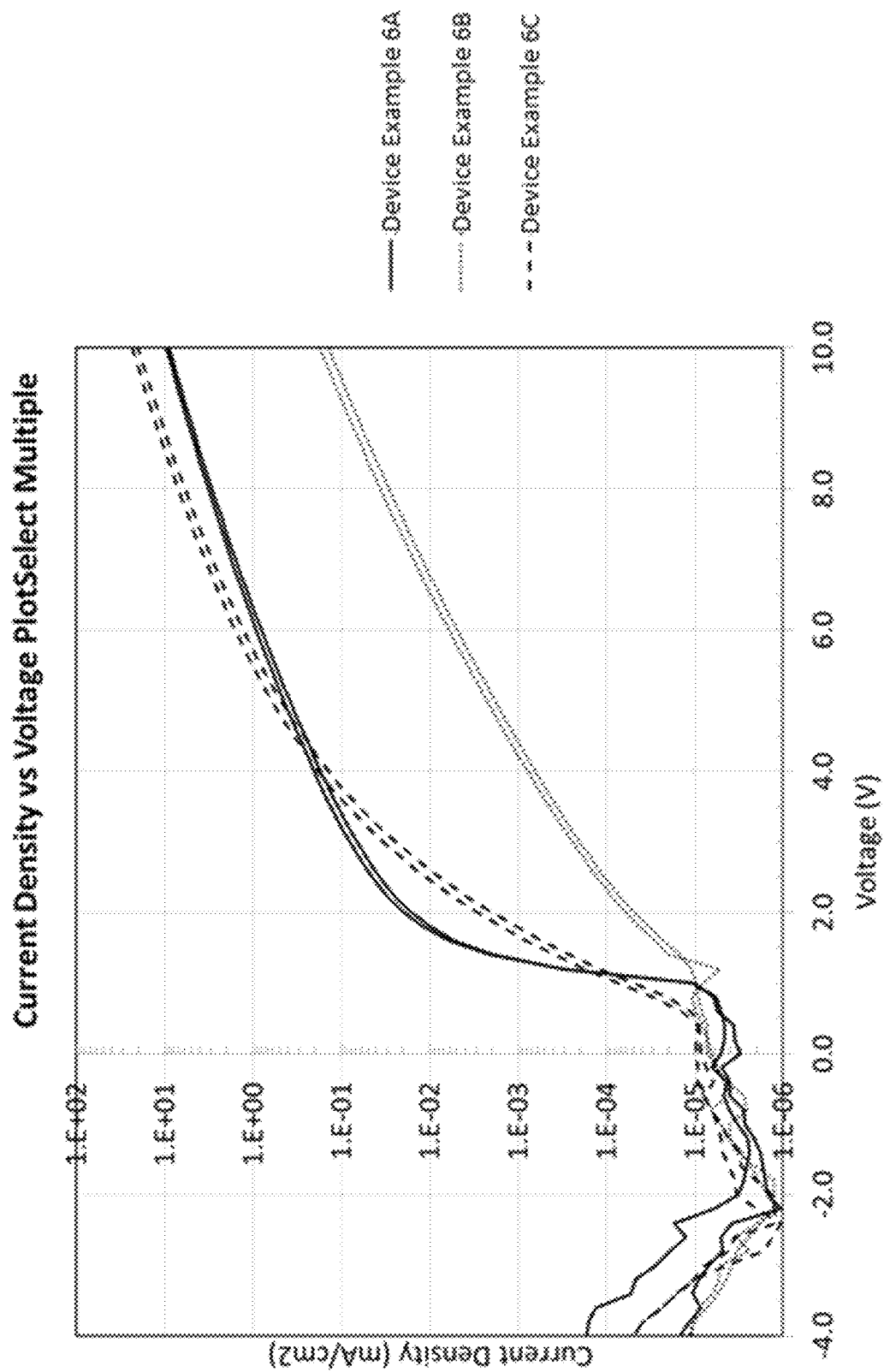
FIG. 19 is a graph of current density vs. voltage for electron-only devices containing Compound Example 1, Compound Example 2 or Compound Example 4.

With reference to FIG. 19, current density using Compound Examples 1 and 2 is higher than that with Compound Example 7. Without wishing to be bound by any theory, the size of the counter cation may affect the doping strength of the dopant.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A compound of formula (I):

(Core)$n$-(X)$m$  (I)

wherein Core is Ar$_z$, wherein Ar in each occurrence independently is a $C_{6-20}$ aryl group that may be unsubstituted or substituted with one or more substituents, and z is at least 1; n is 0 and m is 1, or n is 1 and m is at least 1; and X is a group of formula (II):

(II)

[structure showing benzimidazole-type core with substituents $(R^1)_x$, $R^2$, $R^3$, $(R^5)_y$, $R^4$]

wherein:
$R^1$, $R^4$ and $R^5$ are each independently H or a substituent;
each $R^2$ is independently a $C_{1-40}$ hydrocarbyl;
$R^3$ is H;
one of $R^1$, $R^4$ and $R^5$ is a direct bond or divalent linking group linking the group of formula (II) to Core in the case where n is 1;
x is 0, 1, 2, 3 or 4;
y is 0, 1, 2, 3 or 4; and
the compound of formula (I) is substituted with at least one ionic substituent of formula (III):

-(Sp$^1$)$p$-(A)$q$  (III)

wherein:
in the case where p=1, Sp$^1$ is a spacer group selected from $C_{1-12}$ alkylene wherein one or more non-adjacent C atoms may be replaced with O, S, C=O or COO; and aryl or heteroaryl that may be unsubstituted or substituted with one or more $C_{1-20}$ alkyl groups wherein one or more non-adjacent C atoms of the $C_{1-20}$ alkyl groups may be replaced with O, S, C=O or COO;
A is independently an anion selected from the group consisting of sulfonate and —COO$^-$, or a cation selected from the group consisting of —N(R$^{11}$)$_3^+$; —P(R$^{11}$)$_3^+$, S(R$^{11}$)$_2^+$ and a heteroaromatic cation wherein R$^{11}$ in each occurrence is H or $C_{1-12}$ hydrocarbyl;
p is 0 or 1;
q is 1 if p is 0; and
q is at least 1 if p is 1, the compound of formula (I) further comprising at least one counterion B to balance the charge of the one or more anions or cations A;
and wherein:
n is 0 and at least one occurrence of at least one of $R^1$, $R^4$ and $R^5$ is an ionic substituent of formula (III); or
n is 1 and Core is substituted with one or more ionic substituents of formula (III); or
n is 1, Core is not substituted with an ionic substituent and at least one of $R^1$, $R^4$ and $R^5$ is an ionic substituent of formula (III).

2. A compound according to claim 1 wherein each $R^2$ is independently a $C_{1-12}$ alkyl.

3. A compound according to claim 1 wherein A, which may be the same or different in each occurrence, is selected from the group consisting of sulfonate and —COO$^-$.

4. A compound according to claim 1 wherein each B is Cs$^+$ or an organic cation.

5. A compound according to claim 1 wherein each A is a cation.

6. A compound according to claim 1 wherein n is 0.

7. A compound according to claim 6 wherein at least one $R^1$ and/or at least one $R^4$ is an ionic substituent.

8. A composition comprising an organic semiconductor and a compound according to claim 1.

9. A formulation comprising a composition according to claim 8 and at least one solvent.

10. A formulation according to claim 9 wherein at least one solvent is a polar solvent.

11. A charge transfer salt comprising an organic semiconductor doped with a compound according to claim 1.

12. An organic electronic device comprising a layer comprising a charge-transfer salt according to claim 11.

13. An organic electronic device according to claim 12 wherein the organic electronic device is an organic light-emitting device comprising an anode, a cathode and a light-emitting layer between the anode and the cathode and wherein the layer comprising the charge-transfer salt is an electron injection layer between the light-emitting layer and the cathode.

14. An organic electronic device according to claim 12 wherein the electron injection layer is in contact with the light-emitting layer.

15. The compound according to claim 1 wherein n is 1 and Core is a core group selected from groups of formula Ar$_z$ wherein Ar in each occurrence independently is a $C_{6-20}$ aryl group that may be unsubstituted or substituted with one or more substituents and z is at least 1.

* * * * *